(12) United States Patent
Alfano et al.

(10) Patent No.: US 7,826,878 B2
(45) Date of Patent: Nov. 2, 2010

(54) OPTICAL TOMOGRAPHY USING INDEPENDENT COMPONENT ANALYSIS FOR DETECTION AND LOCALIZATION OF TARGETS IN TURBID MEDIA

(75) Inventors: Robert R. Alfano, Bronx, NY (US); Min Xu, Woodside, NY (US); Mohammed Alrubaiee, New York, NY (US); Swapan Kumar Gayen, Marlboro, NJ (US)

(73) Assignee: Research Foundation of City University of New York, New York, NY (US)

( * ) Notice: Subject to any disclaimer, the term of this patent is extended or adjusted under 35 U.S.C. 154(b) by 1099 days.

(21) Appl. No.: 11/296,831

(22) Filed: Dec. 7, 2005

(65) Prior Publication Data

US 2008/0146897 A1    Jun. 19, 2008

Related U.S. Application Data

(60) Provisional application No. 60/633,412, filed on Dec. 7, 2004.

(51) Int. Cl.
*A61B 5/00* (2006.01)
(52) U.S. Cl. ........................ 600/310; 382/128
(58) Field of Classification Search ................ 600/310, 600/473–478, 160; 356/3.01, 237.1, 622, 356/623
See application file for complete search history.

(56) References Cited

U.S. PATENT DOCUMENTS

| 5,140,463 A | 8/1992 | Yoo et al. |
| 5,142,372 A | 8/1992 | Alfano et al. |
| 5,227,912 A | 7/1993 | Ho et al. |
| 5,371,368 A | 12/1994 | Alfano et al. |
| 5,813,988 A | 9/1998 | Alfano et al. |
| 5,931,789 A | 8/1999 | Alfano et al. |
| 6,665,557 B1 | 12/2003 | Alfano et al. |
| 6,750,964 B2 * | 6/2004 | Levenson et al. ........... 356/326 |

OTHER PUBLICATIONS

M. Xu et al. "Simulated and Experimental Separation and Characterization of Absorptive Inhomogeneities Embedded in Turbid Media," OSA Biomedical Topical Meeting, (Apr. 2004).

(Continued)

*Primary Examiner*—Brian Casler
*Assistant Examiner*—Parikha S Mehta
(74) *Attorney, Agent, or Firm*—The Farrell Law Firm, LLP

(57) ABSTRACT

Disclosed is a system and a method for detecting the presence of one or more objects in a turbid medium, the method including: illuminating at least a portion of the turbid medium with incident light having at least one wavelength which interacts with the one or more objects contained in the turbid medium differently than the incident light interacts with the turbid medium; measuring light that emerges from the turbid medium; and detecting and locating the one or more objects using Independent Component Analysis (ICA) of the emergent light from the turbid medium. The present invention is useful for medical applications, such as for finding and locating, a tumor(s) in body organs, or excised tissues. Moreover, the present invention can be used to locate objects in obscuring medium, such as, mines in shallow coastal water, a plane in fog, military targets under fog, smoke or cloud cover.

23 Claims, 10 Drawing Sheets

OTHER PUBLICATIONS

M. Alrubaiee et al. "Time-Resolved and Quasi-Continuous Wave Three-Dimensional Tomographic Imaging of Objects in Tissue-Like Turbid Media," Femtosecond Laser Applications in Biology, Proceedings of SPIE, vol. 5463, (Apr. 2004).

M. Xu et al. "Information Theory Approach to Detect Small Objects Within Tissue-Like Turbid Media," the $4^{th}$ Inter-institute Workshop on Optical Diagnostic Imaging from Bench to Bedside, National Institutes of Health, Natcher Conference Center, (Sep. 20-22, 2004).

M. Alrubaiee et al. "Three-Dimensional Localization and Reconstruction of Objects in a Turbid Medium Using Independent Component Analysis of Optical Transmission and Fluorescence Measurements," the $4^{th}$ Inter-institute Workshop on Optical Diagnostic Imaging from Bench to Bedside, National Institutes of Health, (Sep. 20-22, 2004).

H. Inaba, "Coherent Detection Imaging for Medical Laser Tomography", Medical Optical Tomography: Functional Imaging and Monitoring, vol. IS11 of SPIE Institute Series, pp. 317-347 (1993).

S. K. Gayen and R. R. Alfano, "Emerging Optical Biomedical Imaging Techniques," Opt. Photon. News 7, 17-22 1996; J. C. Hebden, et al. "Optical Imaging in Medicine: I. Experimental Techniques," Phys. Med. Biol. 42, 825-840 (1997).

S. R. Arridge et al., "Optical Imaging in Medicine: II. Modeling and Reconstruction," Phys Med Biol. 42, 841-853 (1997).

V. Ntziachristos et al., "Experimental Three-Dimensional Fluorescence Reconstruction of Diffuse Media by Use of a Normalized Born Approximation," Opt. Lett. 26, 893-895, (2001).

L. Wang, R. R. Alfano et al., "Ballistic 2-D Imaging Through Scattering Walls Using an Ultrafast Optical Kerr Gate," Science 253, pp. 769-771, (1991).

S. K. Gayen et. al., "Two-Dimensional Near-Infrared Transillumination Imaging of Biomedical Media With a Chromium-Doped Forsterite Laser," Appl. Opt. vol. 37, pp. 5327-5336 (1998).

S. K. Gayen, et. al. "Near-Infrared Laser Spectroscopic Imaging: A Step Towards Diagnostic Optical Imaging of Human Tissues," Lasers in the Life Sciences vol. 37, pp. 187-198, (1999).

S. K. Gayen, et. al., "Time-Sliced Transillumination Imaging of Normal and Cancerous Breast Tissues," in OSA Trends in Optics and Photonics Series vol. 21 on Advances in Optical Imaging and Photon Migration, pp. 63-66, (1998).

J. J. Dolne et. al ,"IR Fourier Space Gate and Absorption Imaging Through Random Media," Lasers in the Life Sciences vol. 6, pp. 131-141, (1994).

J. C. Hebden et.al., "Time Resolved Imaging Through a Highly Scattering Medium," Appl. Opt. vol. 30, pp. 788-794, (1991); and Demos et.al., "Time-Resolved Degree of Polarization for Human Breast Tissue," Opt. Commun. vol. 124, pp. 439-442, (1996).

W. Cai et. al., "Optical Tomographic Image Reconstruction From Ultrafast Time-Sliced Transmission Measurements," Appl. Opt. vol. 38, pp. 4237-4246 (1999).

W. Cai et. al., "Time-Resolved Optical Diffusion Tomographic Image Reconstruction in Highly Scattering Turbid Media," Proc. Natl. Acad. Sci. USA, vol. 93, pp. 13561-13564, (1996).

S. R. Arridge, "The Forward and Inverse Problems in Time-Resolved Infra-red Imaging," published in the Medical Optical Tomography: Functional Imaging and Monitoring, SPIE, vol. IS11, C. Muller ed., pp. 35-63, (1993).

J. R. Singer et. al., "Image Reconstruction of the Interior Bodies That Diffuse Radiation", Science, vol. 248, pp. 990-993, (1993).

M. Xu, M. Lax and R. R. Alfano, "Time-Resolved Fourier Optical Diffuse Tomography," J. Opt. Soc. Am. A, vol. 18, No. 7, pp. 1535-1542, (2001).

W. Cai, M. Lax and R. R. Alfano, "Analytical Solution of the Elastic Boltzmann Transport Equation in an Infinite Uniform Medium Using Cumulant Expansion," J. Phys. Chem. B, vol. 104, No. 16, pp. 3996-4000, (2000).

M. Xu, W. Cai, M. Lax and R. R. Alfano, "Photon-Transport Forward Model for Imaging in Turbid Media," Opt. Lett., vol. 26, No. 14, pp. 1066-1068, (2001).

M. Lax et. al., "Classical Diffusive Photon Transport in a Slab", In Laser Optics of Condensed Matter, Plenum, New York, pp. 229-237, (1987).

R. C. Haskell, et al., "Boundary Conditions for the Diffusion Equation in Radiative Transfer," J. Opt. Soc. Am. A, vol. 11, No. 10, pp. 2727-2741, (1994).

J. F. Cardoso, "Blind Signal Separation: Statistical Principles," Proceedings of the IEEE, vol. 9, No. 10, pp. 2009-2025, (1998).

M. V. Klein, "Optics," John Wiley & Sons, pp. 453-475 (1970).

P. Comon, "Independent Component Analysis—A New Concept?", Signal Processing, vol. 36, pp. 287-314 (1994).

A. J. Bell, "Information Theory, Independent Component Analysis, and Applications", in Unsupervised Adaptive Filtering, vol. I, Wiley, pp. 237-264, (2000).

X. D. Li et. al., "Fluorescent Diffuse Photon Density Waves in Homogeneous and Heterogeneous Turbid Media: Analytic Solutions and Applications", Appl. Opt., vol. 35, No. 19, pp. 3746-3758, (1996).

A. H. Gandjbakhche et. al., "Photon Path-Length Distributions for Transmission Through Optically Turbid Slabs," Phys. Rev. E, vol. 48, No. 2, pp. 810-818, (1993).

H. Heusmarin et. al., "Characterization of Female Breasts In vivo by Time Resolved and Spectroscopic Measurements in Near Infrared Spectroscopy", J. Biomed. Opt., vol. 1, pp. 425-434, (1996).

Hugo J. van Staveren et. al., "Light Scattering in Intralipid-10% in the Wavelength Range of 400-1100 nm", App. Opt., vol. 30, No. 31, pp. 4507-4514, (1991).

D. J. Hall, et al. "Imaging Very-Low-Contrast Objects in Breastlike Scattering Media With a Time-Resolved Method", Appl. Opt., vol. 36, pp. 7270-7276, (1997).

Q. Fu et. al. "High-average-power kilohertz-repetition-rate sub-100-fs Ti:sapphire amplifier system", Opt. Lett, vol. 22, pp. 712-714, (1997).

J.C. Hebden et al., "Optical Imaging in Medicine: I. Experimental Techniques." Phys. Med. Biol. 42, pp. 825-840 (1997).

A.B. Milstein et al., "Fluorescence Optical Diffusion Tomography" Appl. Opt. 42, pp. 3081-3094 (2003).

S. R. Arridge, "Optical Tomography in Medical Imaging", Inverse Problems 15, R41-R93, (1999).

B. B. Das et al. "Ultrafast Time-Gated Imaging in Thick Tissues: A Step Toward Optical Mammography," Opt. Lett. vol. 18 pp. 100,2-100,4 (1993).

S.G. Demos et al., "Time Resolved Degree of Polarization For Human Breast Tissue", Optics Communications 124 pp. 439-442 (1996).

Gayen, R. R. Alfano, "Sensing Lesions in Tissues With Light", Optics Express, 4, pp. 475-480 (1999).

* cited by examiner

OPTICAL TOMOGRAPHY USING INDEPENDENT COMPONENT ANALYSIS FOR DETECTION AND LOCALIZATION OF TARGETS IN TURBID MEDIA

PRIORITY

This application claims priority to a provisional application entitled "Optical Tomography Using Independent Component Analysis For Detection And Localization Of Targets In Turbid Media," which was filed in the U.S. Patent and Trademark Office on Dec. 7, 2004, and assigned Ser. No. 60/633,412, the contents of which are incorporated herein by reference.

GOVERNMENTAL INFORMATION

This invention is supported in part by the U.S. Army Medical Research and Material Command, National Aeronautics and Space Administration, Office of Naval Research.

BACKGROUND OF THE INVENTION

1. Field of the Invention

The present invention relates generally to a system and method for detecting, imaging, and determining the location of objects in a turbid medium using light as a probe, and more particularly relates to a system and method for finding and locating objects including, tumors in living tissue, an individual, a building, or a vehicle such as an aircraft, a missile, etc. located in smoke, fog, and vehicles and objects such as submarines and mines located in shallow and/or murky water using independent component analysis (ICA).

2. Description of the Related Art

With the pervasiveness of cancer and terrorism in modern times, it has become common to screen for undesired objects. For example, it is common to screen the human body for tumors which can include cancerous as well as benign tumors. Moreover, with the pervasiveness of terrorism, it is common to patrol and screen secure areas for objects and individuals that should not be in the secure areas. For example, border crossings, military bases, airports, governmental buildings, high-occupancy buildings and other selected locations are typically under constant surveillance to assure the security of these areas. Finding objects in a turbid medium has been researched in the past. Basic principles and simulation as well as experimental results of finding objects in a turbid medium are known. For example, see M. Xu et al. "Simulated And Experimental Separation And Characterization Of Absorptive Inhomogeneities Embedded In Turbid Media," OSA Biomedical Topical Meeting, April, 2004; M. Alrubaiee et al. "Time-Resolved And Quasi-Continuous Wave Three-Dimensional Tomographic Imaging," Femtosecond Laser Applications in Biology, Proceedings of SPIE, vol. 5463, April, 2004; M. Xu et al. "Information Theory Approach To Detect Small Inhomogeneities Within Tissue-Like Turbid Media," the 4$^{th}$ Inter-institute Workshop on Optical Diagnostic Imaging from Bench to Bedside, National Institutes of Health, Natcher Conference Center, Sep. 20-22, 2004; M. Alrubaiee et al. "Three-Dimensional Localization And Reconstruction Of Objects In A Turbid Medium Using Independent Component Analysis Of Optical Transmission And Fluorescence Measurements," the 4$^{th}$ Inter-institute Workshop on Optical Diagnostic Imaging from Bench to Bedside, National Institutes of Health, Sep. 20-22, 2004, the contents of all of which are incorporated herein by reference.

Additionally, on the medical side, noninvasive optical probing of tumors and functional monitoring of physiological activities in a human body using near infrared (NIR) light has been investigated by many investigators as compiled in G. Muller, R. R. Alfano, et al. Medical Optical Tomography: Functional Imaging and Monitoring, Vol. IS11 of SPIE Institute Series, 1993; S. K. Gayen and R. R. Alfano, "Emerging Optical Biomedical Imaging Techniques," Opt. Photon. News 7, 17-22 1996; J. C. Hebden, et al. "Optical Imaging In Medicine: I. Experimental Techniques," Phys. Med. Biol. 42, 825-840, 1997; S. R. Arridge et al., "Optical Imaging In Medicine: II. Modeling And Reconstruction," Phys Med Biol. 42, 841-853, 1997, the contents of all of which are incorporated herein by reference. While some optical imaging techniques use a difference in light scattering and absorption characteristics between normal and cancerous tissues, other optical image techniques detect fluorescence of externally administered contrast agents that attach selectively to the tumors, or native tissue fluorescence. For example, see Ntziachristos et al., "Experimental Three-Dimensional Fluorescence Reconstruction Of Diffuse Media By Use Of A Normalized Born Approximation," Opt. Lett. 26, 893-895, (2001); A. B. Milstein, et al., "Fluorescence Optical Diffusion Tomography," Appl. Opt. 42, 3081-3094 (2003), the contents of all which are incorporated herein by reference.

Although both direct imaging, for example as disclosed in L. Wang, R. R. Alfano et al., "Ballistic 2-D Imaging Through Scattering Walls Using An Ultrafast Optical Kerr Gate," Science 253, 769-771, 1991, and inverse reconstruction, for example as disclosed in R. Arridge, "Optical Tomography In Medical Imaging," Inverse Problems 15, R41-R93, 1999, approaches have been used to obtain images of a target embedded in various types of turbid media, these methods still leave much to be desired. For example, the direct imaging approach uses different techniques to sort out image bearing ballistic and snake light, and to reject image blurring multiple scattered light in order to obtain a desired image, for example see U.S. Pat. No. 5,140,463, entitled "Method And Apparatus For Improving The Signal To Noise Ratio Of An Image Formed Of An Object Hidden In Or Behind A Semi-Opaque Random Media," to Yoo et. al.; U.S. Pat. No. 5,142,372, to R. R. Alfano et. al., entitled U.S. Pat. No. 5,227,912, entitled "Multiple-Stage Optical Kerr Gate System," to Ho et. al., U.S. Pat. No. 5,371,368, entitled "Ultrafast Optical Imaging Of Objects In A Scattering Medium," to R. R. Alfano et. al.; Gayen and R. R. Alfano, "Sensing Lesions In Tissues With Light," Optics Express Vol. 4, pp. 475-480 (1999); Gayen et. al., "Two-Dimensional Near-Infrared Transillumination Imaging Of Biomedical Media With A Chromium-Doped Forsterite Laser," Appl. Opt. Vol. 37, pp. 5327-5336 (1998); Gayen, et. al. "Near-Infrared Laser Spectroscopic Imaging: A Step Towards Diagnostic Optical Imaging Of Human Tissues," Lasers in the Life Sciences Vol. 37, pp. 187-198, (1999); Gayen, et. al., "Time-Sliced Transillumination Imaging Of Normal And Cancerous Breast Tissues," in OSA Trends in Optics and Photonics Series Vol. 21 on Advances in Optical Imaging and Photon Migration, pp. 63-66, (1998); Dolne et. al, "IR Fourier Space Gate And Absorption Imaging Through Random Media," Lasers in the Life Sciences Vol. 6, pp. 131-141, (1994); Das et. al. "Ultrafast Time-Gated Imaging In Thick Tissues: A Step Toward Optical Mammography," Opt. Lett. Vol. 18, pp. 1002-1004, (1993); Hebden et. al., "Time Resolved Imaging Through A Highly Scattering Medium," Appl. Opt. Vol. 30, pp. 788-794, (1991); and Demos et. al., "Time-Resolved Degree Of Polarization For Human Breast Tissue," Opt. Commun. Vol. 124, pp. 439-442, (1996); the contents of all of which is incorporated herein by reference.

Although the above disclosed methods are typically suitable for turbid mediums whose thickness is less than 10 times the transport-mean-free-path, it is now accepted that for the turbid medium thickness which is greater than 10 times the transport-mean-free-path, direct shadowgram imaging is not feasible, and one has to resort to inverse reconstruction technique.

The conventional inverse reconstruction approach to locate and characterize the targets, matches the detected light intensities on the boundaries to that computed by a forward model of light propagation in the medium. The absorption and scattering coefficient distribution of the full medium is updated iteratively until the emerging light intensities on the boundaries predicted by the forward model are close to the observed values. Various approaches using time-resolved, frequency-domain, or steady-state lasers have been explored for inverse image reconstruction. Examples of inverse reconstruction methods include U.S. Pat. No. 5,813,988, entitled "Time-Resolved Diffusion Tomographic Imaging In Highly Scattering Turbid Media," to R. R. Alfano et. al.; U.S. Pat. No. 5,931,789, entitled "Time-Resolved Diffusion Tomographic 2d And 3d Imaging In Highly Scattering Turbid Media," to R. R. Alfano et. al.; Cai et. al., "Optical Tomographic Image Reconstruction From Ultrafast Time-Sliced Transmission Measurements," Appl. Opt. Vol. 38, pp. 4237-4246 (1999); Cai et. al., "Time-Resolved Optical Diffusion Tomographic Image Reconstruction In Highly Scattering Turbid Media," Proc. Natl. Acad. Sci. USA, Vol. 93, pp. 13561-13564, (1996); U.S. Pat. No. 6,665,557 B1, entitled "Sprectroscopic And Time-Resolved Optical Methods And Apparatus For Imaging Objects In Turbed Media," to R. R. Alfano et. al.; S. R. Arridge, "The Forward And Inverse Problems In Time-Resolved Infrared Imaging," published in the Medical Optical Tomography: Functional Imaging and Monitoring, SPIE, vol. IS11, C. Muller ed., PP. 31-64, (1993); and Singer et. al., "Image Reconstruction Of Interior Bodies That Diffuse Radiation," Science, Vol. 248, pp 990-993, (1993); the contents of each of which are incorporated herein by reference.

SUMMARY OF THE INVENTION

Typical three-dimensional inverse reconstruction approaches suffer from the following limitations. Firstly, the iterative inverse reconstruction approach is time-consuming and not applicable to real-time imaging; and secondly, the spatial resolution in tissues is moderate and there is an inability to discern small targets with a size of less than 5 mm, such as, tumors at an earlier stage deep within the tissue. This limitation can be attributed to the following reasons: (1) light is highly scattered in tissue; and (2) the perturbation of the emerging light intensities due to the presence of targets is weak. Thus, the inverse reconstruction is highly ill-posed and requires regularization to stabilize the inversion at the cost of losing resolution. Moreover, a weak signal from a target is hard to differentiate using conventional methods.

Accordingly, there is a need for a system and a method for detecting and locating a target in a turbid medium, which can overcome the limitation of current inverse reconstruction methods.

Accordingly, it is an object of the present invention to provide a system and a method for detecting and locating a target in a turbid medium, which can overcome the limitations of conventional imaging systems.

It is also an object of the present invention to provide a system and method for detecting, imaging, and determining the location of objects in a turbid medium such as smoke, fog, living tissue, etc. using light as a probe, the objects including, tumors (e.g., benign or cancerous) in living tissue (e.g., an organ, flesh, etc.), an individual, a building, or a vehicle such as an aircraft, a missile, etc. located in an obscuring atmosphere such as dense smoke, fog, hail, rain, snow, and vehicles and objects such as submarines and mines located in shallow and/or murky water using independent component analysis (ICA).

The present invention to uses a technique known as OPtical Tomography using Independent Component Analysis (OPTICA) to detect and localize targets in turbid media that and can overcome limitations of conventional inverse reconstruction methods and can provide millimeter resolution.

Accordingly, it is an object of the present invention to provide a method for detecting the presence of one or more objects in a turbid medium, the method including: illuminating at least a portion of the turbid medium with incident light having at least one predetermined wavelength which interacts with the one or more objects differently than the light interacts with the turbid medium; capturing and measuring light that emerges from the turbid medium; and detecting and locating the one or more objects using Independent Component Analysis (ICA) of light emergent from the turbid medium.

It is a further object of the present invention to provide a method wherein, the light emerging from the turbid medium has the same wavelength as the incident light; the emergent light is detected using a light detector comprising one of a CCD camera, a near-infrared area camera, a one-dimensional array of detectors, photodiodes, photomultiplier tubes, and a streak camera; the detected light is analyzed using Independent Component Analysis (ICA) to determine independent components; and the location of the one or more objects is obtained based on the independent components.

It is also an object of the present invention to provide a method whereby the emergent light includes a plurality of wavelengths at least one of the wavelengths being different from the at least one wavelength of the incident light, signal at different wavelengths are compared using comparisons (such as addition, subtraction, division) which are thereafter used to obtain diagnostic information for indicating whether a target is a tumor and can be further used to determine whether the tumor is benign or cancerous.

It is yet a further object of the present invention to provide a method, wherein the illuminating light includes at least one of a light pulse, continuous-wave light, and amplitude modulated light, laser light having a wavelength between 750 and 950 nm, 950 and 1150 nm, 700 and 1500 nm, and/or 1150 and 1500 nm range. The illuminating light can include light generated by a laser such as a Ti:sapphire laser, a Nd:YAG laser, a dye laser, a semiconductor laser, a solid-state laser, a Cr4+-based laser, a semiconductor laser, and a color-center laser. It is also an object of the present invention to produce light having a variable wavelength using a variable-wavelength laser.

It is also an object of the present invention to provide a system and a method for detecting one or more objects including an absorptive target having an absorption coefficient different from the turbid medium, a scattering target having have a scattering coefficient different from the turbid medium, and/or an emissive target emitting light having at least one wavelength which is different than the wavelength of the incident light. It is also an object of the present invention to detect the emissive targets using extrinsic and/or intrinsic fluorophores.

It is a further object of the presenting invention to provide a system and a method for attenuating noise due to at least one of multiple scattered light and ambient background by using a gating method which can include space gating, Fourier gating, time gating, polarization gating, confocal gating, nonlinear optical gating, and coherence gating. The time gating being optionally provided by an electronically controlled timed gate which can be used for the time gating. The electronically controlled time gate further including one of an ultrafast gated intensified camera system (UGICS) having a gated image intensifier coupled to a charge-coupled-device (CCD) camera, or other suitable device. Furthermore, the duration and position of the time gate can be variably controlled. In yet other embodiments, the time gating is provided by gates which can include an optical Kerr gate, a second harmonic generation cross correlation gate, a four-wave mixing gate, and an upconversion gate.

Accordingly, it is an object of the present invention to provide a system for detecting the presence of one or more objects in a turbid medium, the system including a light source for illuminating at least a portion of the turbid medium with incident light having at least one predetermined wavelength which interacts with the one or more objects differently than the light interacts with the turbid medium; an image capture device for capturing and measuring light that emerges from the turbid medium; and a processor for detecting the presence and determining the location of the one or more objects using Independent Component Analysis (ICA) of the emergent light from the turbid medium, wherein the light emerging from the turbid medium can have at least one wavelength which is the same as, or different from, a wavelength of the incident light and the emergent light is detected using a light detector (or other image capturing device such as a CCD camera, a near-infrared area camera, a one-dimensional array of detectors, photodiodes, photomultiplier tubes, and a streak camera); the processor being further used for analyzed the detected light using Independent Component Analysis (ICA) to determine independent components, and determining the location of the one or more objects is obtained using knowledge of the independent components.

It is yet another object of the present invention to provide a system for detecting the presence of a tumor in a body organ formed of another type of tissue, the system including: a light source for illuminating at least a portion of the body organ with incident light having at least one predetermined wavelength which interacts with the tumor differently than the way it interacts with the tissue in the body organ; an image capture device for capturing and measuring light that emerges from the turbid medium, the turbid medium at least partially surrounding the tumor; and a processor for detecting the presence and determining the location of the tumor using Independent Component Analysis (ICA) of the emergent light from the turbid medium.

BRIEF DESCRIPTION OF THE DRAWINGS

The above and other objects, features and advantages of the present invention will be more apparent from the following detailed description taken in conjunction with the accompanying drawings, in which.

DESCRIPTION OF THE PREFERRED EMBODIMENT

Figure 1:
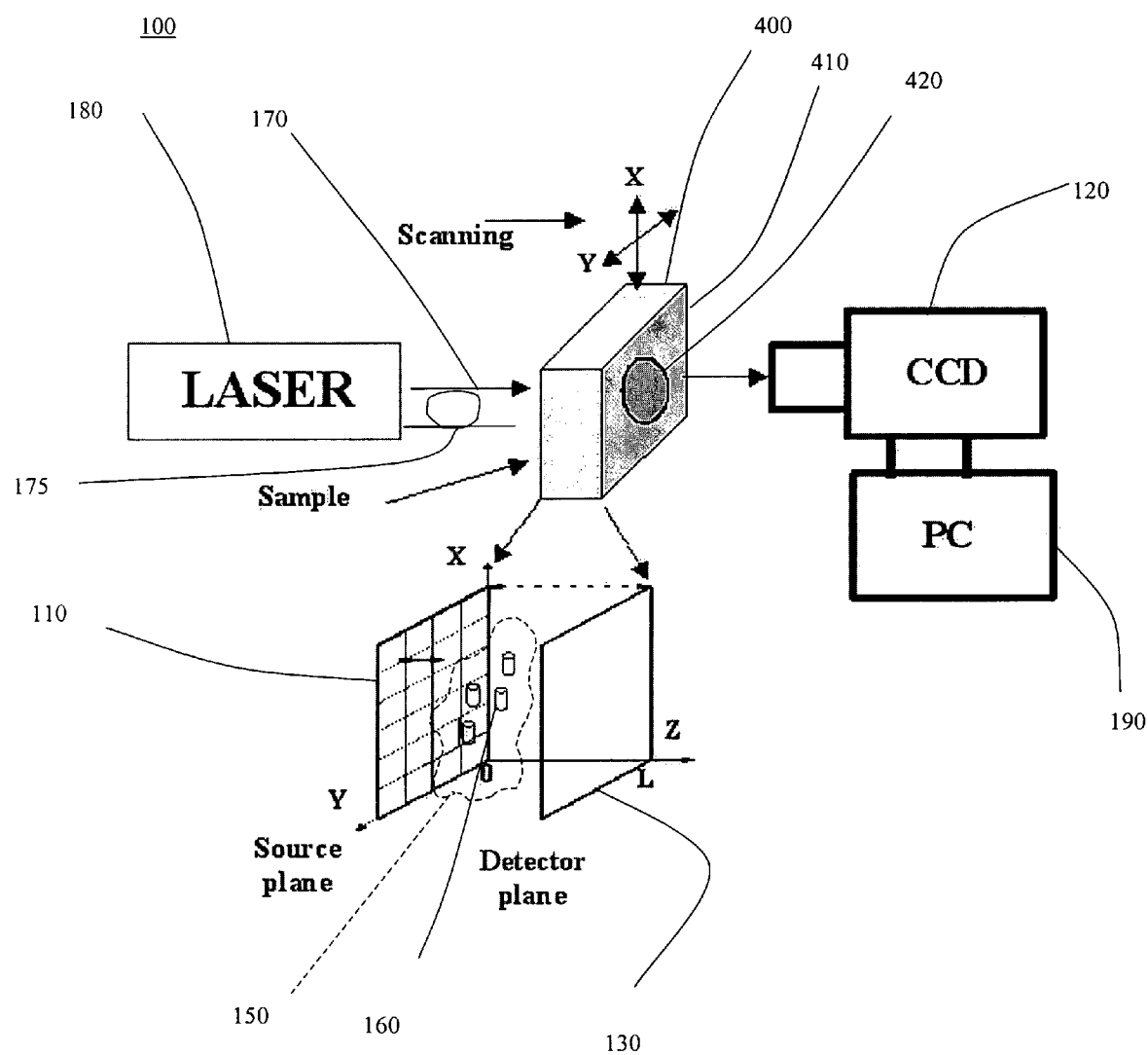
FIG. 1 is a diagram of the experimental arrangement according to an embodiment of the present invention for imaging objects embedded in a turbid medium including a 2-D array in the input plane that is scanned across the incident laser beam.

According to the present invention, optical tomographic imaging of objects in a highly scattered turbid media is provided using an Optical Imaging (OPT) technique and an Independent Component Analysis (ICA) technique to provide a technique known as OPTICA which can provide for the optical tomographic imaging of objects in a highly scattering turbid medium. According to the present invention, an object located in a highly scattered turbid medium, such as a tumor in a human breast tissue, can be determined with an accuracy of 1 mm. The OPTICA technique can use a multiple-source illumination and multiple detector data acquisition scheme as will be explained below.

According to the present invention, a multi-source illumination is used to scan a sample in the xy plane across the incident beam propagating in the z-direction and multiple detectors, for example a charge-coupled device (CCD) camera wherein each pixel of the CCD may be viewed as a detector, are used to locate the objects. The resulting spatial diversity and multiple angular observations provide robust data for extracting three-dimensional location information about the embedded targets (i.e., inhomogeneities) in the medium with a millimeter scale accuracy. The data can be analyzed using an Independent Component Analysis (ICA) of information theory. ICA of the light intensity distribution at the detection plane identifies the major components (which represent the embedded targets) contributing to the intensity distribution data. Using this scheme, every target may be looked upon as a secondary light emitter.

A salient feature of OPTICA is that ICA provides independent components due to the targets, with minimal processing of the data and the ICA does not have to resort to any specific light propagation model for obtaining this information. Specific light propagation models are necessary only in a later stage to determine location (of the targets) by curve fitting of Green's functions as will be described below. OPTICA is also not model specific, since any appropriate model for light propagation including a diffusion approximation or a radiative transfer equation may be used. Another advantage is that OPTICA can be used with light scattering and/or absorbing targets, as well as with fluorescent targets where the fluorophore may be extrinsic or intrinsic.

An advantage of the OPTICA method is that it can be used with data acquired from objects of different types of geometric shapes, such as, slabs, cylinders, spheres, and/or arbitrary shaped boundaries. The OPTICA approach as taught by the present invention is fast, and amenable to near real-time detection and localization of objects in a turbid medium, which is a key consideration for in vivo medical imaging. The approach disclosed herein is remarkably sensitive, and can detect a 5-mm diameter and a 5-mm long cylindrical target, at least one of having a reduced scattering coefficient, which is only 10% higher than the surrounding medium, in a 166-mm long, 82-mm wide, and 55-mm thick slab made of materials having a reduced scattering coefficient $\mu_s$, ~0.9 mm$^{-1}$ (transport length, $l_t$ ~1.1 mm), and an absorption coefficient, $\mu_a$ ~0006 mm$^{-1}$. Conventionally, such objects were considered improbable to be detected (e.g., see J. Hall et al., "Imaging Very-Low-Contrast Objects In Breastlike Scattering Media With A Time-Resolved Method", Appl. Opt., vol. 36, pp. 7270-7276, 1997)).

OPTICA is suitable for imaging small targets. For example, OPTICA can be used to detect small objects (e.g., objects with a size of ~1 mm) in a highly scattering medium. Given its ability to identify low-contrast small objects, the present invention is suitable for imaging and detecting early, as well as later, -stage tumors in living tissue and body organs, which can be especially beneficial when dealing with cancerous tumors.

Theoretical formalisms and algorithms of OPTICA taught by the present invention will now be provided. OPTICA is an information theory approach to detect and locate objects within a turbid medium. For the sake of clarity a detailed description of well known principles will not be given, when it may obscure the present invention.

An exploded perspective view block diagram illustrating an OPTICA scanning system including a sample according to the present invention is shown in FIG. 1. OPTICA uses a multi-source illumination and multi-detector signal acquisition scheme providing a variety of spatial and angular views essential for three-dimensional (3-D) object localization. The multi-source illumination can be realized by scanning an input surface (or, a source plane) 110 across an incident beam 170 in a two-dimensional (2-D) array of points (e.g., $x_{s_k}$, $y_{s_k}$; k=1, 2, ..., n). Alternatively, the input surface may be kept fixed, and a beam of light may be scanned. Corresponding to illumination of the k-th grid point on the source plane 110, a charge-coupled device (CCD) camera 120 records the spatial intensity distribution, $I_k(x_d, y_d)$, on the exit surface (or, detector plane) 130. Thus, every pixel of the CCD camera 120 can function as a detector implementing the multi-detector measurement arrangement. The difference between the above-mentioned spatial intensity distribution, $I_k(x_d, y_d)$ and an estimated background (for example, an averaged intensity distribution obtained from different source scanning positions) provides the perturbation in the spatial intensity distribution in the detector plane for illumination at the k-th grid point, $\Delta I_k(x_d, y_d)$. The different source and scanning positions can be created using a light emitting diode (LED) LASER array (not shown). Additionally, one or more lasers 180, can be used with steering optics to guide an incident beam 170 to predetermined locations. A fiber optic guide 175 can also be used to channel the incident beam 170.

A localization algorithm is based on the premise that each object (or, target 160) within the turbid medium 150 alters the propagation of light through the turbid medium 150. Consequently, the spatial distribution of the light intensity at a detector plane of the turbid medium 150 is different with embedded targets or objects (e.g., target 160) than that without them. The influence of an object on the light intensity distribution $\Delta I_k(x_d, y_d)$ involves propagation of light from the source to the object, and from the object to the detector, and can be described in terms of two Green's functions (propagators): the first $G(r, r_s)$ describing light propagation from a source $r_s$ to an object r; and the second $G(r_d, r)$ from the object r to the detector at $r_d$. In order to correlate perturbations in the light intensity distributions $\Delta I_k(x_d, y_d)$, with the objects embedded in the turbid medium, these objects illuminated by the incident wave are assumed to be "virtual sources", and light intensity distribution $\Delta I_k(x_d, y_d)$ assumed to be a weighted mixture of signals arriving from the virtual sources to the detector plane. ICA assumes these "virtual sources" to be independent, and based on this assumption provides the independent components of the virtual sources. The number of leading independent components is the same as the number of the embedded objects. The effective contributions of the independent components to the light intensity distribution on the source and detector planes are proportional to the projection of the Green's functions $G(r, r_s)$ and $G(r_d, r)$, on the source and detector planes, respectively. The location and characteristics of the objects are obtained from fitting either or both of the projections of the Green's functions to those of the model Green's function in a background medium.

In a linearized scheme of inversion, the perturbation of the detected light intensities on the boundaries of the medium, the scattered wave field, due to absorptive and scattering objects (i.e., inhomogeneities) can be defined by a diffusion approximation (DA) shown in Equation 1 below. Diffusion approximations are further defined in Xu, M. Lax and R. R. Alfano, "Time-Resolved Fourier Optical Diffuse Tomography," J. Opt. Soc. Am. A, vol. 18, no. 7, pp. 1535-1542, (2001), the contents of which are incorporated herein by reference.

$$\phi_{sca}(r_d, r_s) = -\int d^3r G(r_d, r) \delta\mu_a(r) c G(r, r_s) - \int d^3r \delta D(r) c \nabla_r G(r_d, r) \cdot \nabla_r G(r, r_s) \quad (1)$$

When illuminated by a unit point source, where $r_s$, r, and $r_d$ are the positions of the source, the inhomogeneity or object, and the detector, respectively, $\delta\mu_a = (\mu_{a,obj} - \mu_a)$ and $\delta D = (D_{obj} - D)$ are the differences in an absorption coefficient and a diffusion coefficient, respectively, between the inhomogeneity and the background, c is the speed of light in the medium, and G(r,r') is a Green's function describing light propagation from r' to r inside the background turbid medium of absorption coefficient $\mu_a$ and diffusion coefficient D. It is noted that the explicit dependence on the modulation frequency of the incident wave in the frequency domain in Equation 1 has been omitted for the sake of clarity. The following formalism can be applied to continuous wave, frequency-domain and time-domain measurements. The time domain measurement is first Fourier transformed over time to obtain data over many different frequencies. Although Equation 1 includes a DA, it should be emphasized that the invention is not limited to a DA, but can be used with other models of light propagation in a turbid media, such as, a cumulant approximation (e.g., see W. Cai, M. Lax and R. R. Alfano, "Analytical Solution Of The Elastic Boltzmann Transport Equation In An Infinite Uniform Medium Using Cumulant Expansion," J. Phys. Chem. B, vol. 104, no. 16, pp. 3996-4000, (2000); and M. Xu, W. Cai, M. Lax and R. R. Alfano, "A Photon Transport Forward Model For Imaging In Turbid Media," Opt. Lett., vol. 26, no. 14, pp. 1066-1068, (2001)), a random walk model (e.g., see H. Gandjbakhche et. al., "Photon Path-Length Distributions For Transmission Through Optically Turbid Slabs," Phys. Rev. B, vol. 48, no. 2, pp. 810-818, (1993, the contents of each of which are incorporated herein by reference) and linearized radiative transfer models.

The Green's function G for a slab geometry in the diffusion approximation is given by $$G(r, r') \equiv G(\rho, z, z') = \frac{1}{4\pi D} \sum_{k=-\infty}^{\infty} \left[ \frac{\exp(-kr_k^+)}{r_k^+} - \frac{\exp(-kr_k^-)}{r_k^-} \right]; \quad (2)$$

where $$r_k^\pm = \sqrt{\rho^2 + (z \mp z' \pm 2kd)}$$

for an incident amplitude-modulated wave of modulation frequency $\omega$, where $k=0, \pm 1, \pm 2, \ldots,$ $$\rho = \sqrt{(x-x')^2 + (y-y')^2}$$

is the distance between the two points $r=(x,y,z)$ and $r'=(x',y',z')$ projected onto the xy plane, $$k = \sqrt{(\mu_a - i\omega/c)/D}$$

chosen to have a nonnegative real part, and extrapolated boundaries of the slab are located at $z=0$ and $z=d=L_z+2z_e$, respectively, where $L_z$ is a physical thickness of the slab and an extrapolation length $z_e$ should be determined from a boundary condition of the slab (e.g., see Lax et. al., "Classical Diffusion Photon Transport In A Slab, In Laser Optics Of Condensed Matter," Plenum, New York, pp. 229-237, (1987); and R. C. Haskell, et al., "Boundary Conditions For The Diffusion Equation In Radiative Transfer," J. Opt. Soc. Am. A, vol. 11, no. 10, pp. 2727-2741, (1994) the contents of each of which are incorporated herein by reference). Equation 2 serves as the model of Green's function in the uniform background medium of a slab geometry. The modulation frequency $\omega=0$ for a continuous wave light. The Green's function for the slab in time domain is the inverse Fourier transform of Equation 2 in a frequency domain.

In practice, the projections of the Green's function on the source and detector planes, are determined from the measured perturbations in the light intensity distribution using ICA according to the present invention. The comparison to the prototype Green's function is then used to locate and characterize the inhomogeneities. The formalism given is for absorptive, scattering and fluorescent targets are detailed in the following subsections.

Under the assumption that absorptive targets are localized, the jth one is contained in volume $V_j$ centered at $r_j$ (where 1 j J), the scattered wave field $\phi_{sca}(r_d,r_s)$ of Equation 1 can be rewritten as:

Error! Objects cannot be created from editing field codes (3)

where $q_j = \delta\mu_a(r_j)cV_j$ is the absorption strength of the jth target, and $r_j$ is the position of the jth target. The scattered wave may be interpreted as an instantaneous linear mixture (e.g., see J. F. Cardoso, "Blind Signal Separation: Statistical Principles," Proceedings of the IEEE, vol. 9, no. 10, pp. 2009-2025, (1998) the contents of which is incorporated herein by reference).

$$x(r_s) = As(r_s) \quad (4)$$

In Equation 4 separated virtual sources $s(r_s)=(q_1 G(r_1,r_s), \ldots, q_J G(r_J,r_s))^T$ represents the J virtual sources, i.e., the J targets illuminated by the incident wave. A is a mixing matrix given by Equation 5.

$$A = \begin{pmatrix} G(r_{d_1}, r_1) & G(r_{d_1}, r_2) & \ldots & G(r_{d_1}, r_j) \\ G(r_{d_2}, r_1) & G(r_{d_2}, r_2) & \ldots & G(r_{d_2}, r_j) \\ \vdots & \vdots & \ddots & \vdots \\ G(r_{d_m}, r_1) & G(r_{d_m}, r_2) & \ldots & G(r_{d_m}, r_j) \end{pmatrix} \quad (5)$$

whose jth column (which is a mixing vector) provides weight factors for the contributions from the jth absorbtive target to the detectors, and a multi-source multi-detector set $x(r_s) = ((\phi_{sca}(r_{d_1},r_s), \ldots, -\phi_{sca}(r_{d_m},r_s))^T)$ is an observed light intensity change where the superscript "T" denotes a transposition. The observation is made over m positions $r_{d_1}, \ldots, r_{d_m}$. The incident light source scans a total of n positions $r_{s_1}, \ldots, r_{s_n}$, sequentially, which can be regarded as "temporal" sampling points in the instantaneous linear mixture model of Equation 4. The multi-source multi-detector data set x(r) thus describes signals observed in m channels (i.e., m detectors) from J virtual sources (or J absorbtive targets) simultaneously over n discrete "temporal" points (n spatial scanning points). A single absorptive target is represented by a single virtual source $q_j G(r_j,r_s)$. The virtual source $q_j G(r_j,r_s)$ represents the individual absorbtive target illuminated by the incident wave and is similar to the concept of the secondary source in Huygen's principle (e.g., see M. V. Klein, "Optics," John Wiley & Sons, (1970)). The role of detectors and sources can be interchanged due to the reciprocal property of light propagation.

The principal assumption of the above-stated formalism is that the jth absorptive target (treated as virtual source $q_j G(r_j,r_s)$) is independent of the virtual sources at other locations. Under this assumption, ICA can be used with the observations from the light source scanned at n>>J positions to separate out both virtual sources $s(r_s)$ and the mixing matrix A (e.g., see P. Comon, "Independent Component Analysis—A New Concept?", Signal Processing, vol. 36, pp. 287-314 (1994) and J. F. Cardoso, "Blind signal separation: Statistical Principles", Proceedings of the IEEE, vol. 9, no. 10, pp. 2009-2025, (1998), the contents of each of which is incorporated herein by reference).

ICA is a statistical approach to separate independent sources from linear instantaneous or convolutive mixtures of independent signals without relying on any specific knowledge of the sources except that they are independent. The sources are recovered by a minimization of a measure of dependence, such as mutual information (e.g., see P. Comon, "Independent Component Analysis—A New Concept?", Signal Processing, vol. 36, pp. 287-314 (1994); and A. J. Bell, "Information Theory, Independent Component Analysis, and Applications", in Unsupervised Adaptive Filtering, Vol. 1, Wiley, pp. 237-264, (2000), the contents of each of which is incorporated herein by reference) between the reconstructed sources (e.g., see J. F. Cardoso, "Blind Signal Separation: Statistical Principles", Proceedings of the IEEE, vol. 9, no. 10, pp. 2009-2025, (1998), the contents of which are incorporated herein by reference). The recovered virtual sources and mixing vectors from ICA are unique up to permutation and scaling.

The two Green's functions of light propagating from the source to the target (i.e., $G(r,r_s)$) and from the target to the detector (i.e., $G(r,r_d)$) are retrieved from the separated virtual sources $s(r_s)$ and the mixing matrix A. The jth element $s_j(r_s)$ of the virtual source array and the jth column $a_j$ (mixing vector) of the mixing matrix A provide scaled projections of the Green's function on the source and detector planes, $G(r_j,r_s)$ and $G(r_d,r_j)$, respectively. $s_j(r_s)$ and $a_j$ can be defined as:

$$s_j(r_s) = \alpha_j G(r_j, r_e); \text{ and}$$

$$a_j = \beta_j G(r_d, r_j), \quad (6)$$

where $\alpha_j$ and $\beta_j$ are scaling constants for the jth target.

Both the location and strength of the jth target can be computed by a simple fitting procedure using Equation 6. For example, a least square fitting procedure given by Equation (7)

$$\min_{r_j, \alpha_j, \beta_j} \left\{ \sum_{r_s} [\alpha_j^{-1} s_j(r_s) - G(r_j, r_s)]^2 + \sum_{r_s} [\beta_j^{-1} a_j - G(r_d, r_j)]^2 \right\} \quad (7)$$

can be used. The fitting procedure yields the location $r_j$ of, and the two scaling constants $\alpha_j$ and $\beta_j$ for, the jth absorptive target whose absorption strength is then given by $q_j = \alpha_j \beta_j$.

For scattering targets, under the assumption that the targets are localized in a few regions, an analysis which is similar to the analysis of absorptive targets can be used. Up to three virtual sources may appear for a single scattering target corresponding to the x, y, and z components in the dot product $\nabla_r G(r_d,r) \cdot \nabla_r G(r,r_s) = {}_x G(r_d,r)_x G(r,r_s) + {}_y G(r_d,r)_y G(r,r_s) + {}_z G(r_d,r)_z G(r,r_s)$ shown in Equation 1.

By introducing two auxiliary functions as shown in Equations 8 and 9 below, $$g_\perp(r, r') = \frac{1}{4\pi D} \sum_{k=-\infty}^{+\infty} \left[ (kr_k^+ + 1) \frac{\exp(-kr_k^+)}{(r_k^+)^3} - (kr_k^- + 1) \frac{\exp(-kr_k^-)}{(r_k^-)^3} \right] \quad (8)$$

$$g_z(r, r') = \frac{1}{4\pi D} \sum_{k=-\infty}^{+\infty} \left\{ (z - z' + 2kd)(kr_k^+ + 1) \frac{\exp(-kr_k^+)}{(r_k^+)^3} - (z + z' - 2kd)(kr_k^- + 1) \frac{\exp(-kr_k^-)}{(r_k^-)^3} \right\}, \quad (9)$$

the scattered wave due to scattering targets can be rewritten as:

$$\phi_{sca}(r_d,r_s) = -d^3 r \delta D(r) c \{ [(x-x_d)(x-x_s) + (y-y_d)(y-x_s)]g(r,r_d)g(r,r_s) + g_z(r,r_d)g_z(r,r_s) \}. \quad (10)$$

By denoting the scattering targets as $q_j' = \delta D(r_j) c V_j'$ where c is the speed of light in the medium, an $V_j'$ is the volume of the jth scattering target, the scattered wave field can be transformed to:

$$\phi_{sca}(r_d, r_s) = \sum_{j=1}^{n'} g_z(r_j, r_d) q_j' g_z(r_j, r_s) + \quad (11)$$

$$\sum_{j=1}^{n'} \rho_{dj} \cos\theta_\perp(r_j, r_d) q_j' \rho_{sj} \cos\theta_s g_\perp(r_j, r_s) +$$

$$\sum_{j=1}^{n'} \rho_{dj} \sin\theta_\perp(r_j, r_d) q_j' \rho_{sj} \sin\theta_s g_\perp(r_j, r_s)$$

where $$\rho_{dj} = \sqrt{(x_d - x_j)^2 + (y_d - y_j)^2},$$

$$\rho_{sj} = \sqrt{(x_s - x_j)^2 + (y_s - y_j)^2}$$

and $\theta_d$ and $\theta_s$ are the azimuth angles of $r_d - r_j$ and $r_s - r_j$, respectively. This scattered wave can be regarded as a mixture of contributions from $(3J')$ virtual sources:

$$q_j' g_z(r_j,r_s), q_j' \rho_{sj} \cos\theta_s g(r_j,r_s), \text{ and, } q_j' \rho_{sj} \sin\theta_s g(r_j,r_s), \quad (12)$$

with the respective mixing vectors $$g_z(r_j,r_d), \rho_{dj} \cos\theta_d g(r_j,r_d), \text{ and, } \rho_{dj} \sin\theta_d g(r_j,r_d), \quad (13)$$

where $1 \leq j \leq J$. Generally, there are three virtual sources of specific patterns (e.g., one centrosymmetric pattern and two dumbbell shaped patterns) associated with a single scattering target, whereas only one centrosymmetric virtual source is associated with a single absorptive target. This difference may be used to discriminate absorptive and scattering targets. However, for scattering target deep within a turbid media, only the $q_j' g_z(r_j,r_s)$ virtual source remains significant and the other two virtual sources (i.e., $q_j' \rho_{sj} \cos\theta_s g(r_j,r_s)$, and, $q_j' \rho_{sj} \sin\theta_s g(r_j,r_s)$) are substantially attenuated. In such a situation, other corroborative evidences such as multi-wavelength measurements are required to determine the nature of targets. Both the location and strength of the jth scattering object are computed by fitting the retrieved virtual sources and mixing vectors to Equations 12 and 13, respectively.

The light propagation in a highly scattering medium with embedded fluorescent targets (e.g., intrinsic and/or exogenous contrast agents) excited by an external light source can be described by coupled diffusion equations at the excitation and emission wavelengths (e.g., see M. S. Patterson and B. W. Pogue, "Mathematical Model For Time-Resolved and Frequency-Domain Fluorescence Spectroscopy In Biological Tssues", Appl. Opt., vol. 33, no. 10, pp. 1963-1974, (1994); and Adam B. Milstein et. al. "Fluorescence Optical Diffusion Tomography", Appl. Opt., vol. 42, no. 16, pp. 3081-3094, (2003), the contents of each of which are incorporated herein by reference). A fluorescence signal $U_m(r_d, r_s, \omega)$ can be expressed in terms of the two Green's functions $G_x(r,r_s,\omega)$ and $G_m(r_d,r,\omega)$ describing the light propagation from the source $r_s$ to a fluorophore at r at an excitation wavelength $\lambda_x$ and the light propagation from the fluorophore to the detector at $r_d$ at a transmission wavelength $\lambda_m$, respectively where $\omega$ is the angular modulation frequency of the light as shown in Equation 14 below (e.g., see X. D. Li et. al., "Fluorescent Diffuse Photon Density Waves In Homogeneous And Heterogeneous Turbid Media: Analytic Solutions and Applications", Appl. Opt., vol. 35, no. 19, pp. 3746-3758, (1996) the contents of which are incorporated herein by reference).

Accordingly, a fluorescence signal can be defined by:

$$U_m(r_d, r_s, \omega) = \int G_m(r_d, r, \omega) \frac{\gamma(r)c}{1 - j\omega\tau(r)} G_x(r, r_s, \omega) dr \quad (14)$$

Assuming a unit point illumination source located at $r_s$ and a single exponent decay model of fluorescence with a lifetime of $\tau(r)$. The subscripts x and m denote the quantities associated with the excitation and emission wavelengths, respectively, and c is the speed of light in the medium. A fluorescent yield $y(r)=\eta\mu_{af}(r)$ is a product of the fluorophore's quantum efficiency $\eta$ (which depends upon the type of the fluorophore and chemical environment) and the flororphore's absorption coefficient $\mu_{af}(r)=\eta(r)\sigma_a$, where $\eta(r)$ is the fluorophore concentration and $\sigma_a$ is the known fluorophore absorption cross section at the excitation wavelength. The nonlinear effect due to multiple passages of light through fluorophores can be incorporated into Equation 14 using a nonlinear correction factor if necessary. In the case of multiple fluorescent targets within the medium, it is preferable to rewrite Equation 14 as a summation shown in Equation 15 below.

$$U_m(r_d, r_s, \omega) = \sum_i G_m(r_d, r_i, \omega) q_i(\omega) G_x(r_i, r_s, \omega), \quad (15)$$

where the fluorescence strength $q_i(\omega)=\gamma(r_i)cV_i/(1-j\omega T(r_i))$ and $r_i$ is the location of the ith fluorescent target of volume $V_i$. Equation 15 casts again the fluorescence signal to a mixture of contributions from virtual sources where the virtual source is proportional to $q_i G_x(r_i,r_s,\omega)$ and the mixing matrix is proportional to $G_x(r_d,r_i,\omega)$. The virtual sources are statistically independent. By seeking the maximal mutual independence, the virtual sources can be separated with independent component analysis of observations made from a multi-detector array outside the medium produced by an external scanning point source. Both the location and strength of the fluorophores can be obtained by comparing the virtual source and mixing matrix to the respective Green's functions, in the exactly same procedure outlined for absorptive targets.

An exemplary fluorescent target will now be used to illustrate how the size and shape of a target can be estimated according to an embodiment of the present invention. Once one fluorescent target is located and centered at $r_i$ the fluorescent target's contribution to the fluorescence signal is given by:

$$U_{m_i}(r_d, r_s, \omega) = \frac{\gamma_i(c)}{1 - j\omega\tau} \int_{V_i} G_m(r_d, r, \omega) G_x(r, r_s, \omega) dr, \quad (16)$$

where the integration is performed within an ith fluorescent target assuming uniform fluorescent yield $\gamma_i$ and lifetime $r_i$. To estimate the shape of the fluorescent target, the volume $V_i$ is further projected in the longitudinal direction to its transverse cross section $S_i$ and thickness of the fluorophore $\Delta z_i(\rho)$ is introduced. Accordingly, Equation 16 can be rewritten as shown in Equation 17 below.

$$U_{m_i}(r_d, r_s, \omega) = \quad (17)$$
$$\frac{\gamma_i c}{1 - j\omega\tau_i} \int_{S_i} G_m(\rho_d - \rho, \omega) \Delta z_i(\rho) G_x(\rho - \rho_s, \omega) d\rho$$

where $\rho_d$, $\rho$, and $\rho_s$, are transverse coordinates of a detector, the fluorescent target, and the source, respectively. The weighted convolution of Equation 17 in $\rho$ can be further simplified as shown in Equation 18 below.

$$U_{m_i}(q_d, q_s, \omega) = \frac{\gamma_i c}{1 - j\omega\tau_i} G_m(q_d, \omega) \Delta z_i(q_d + q_s) G_x^*(q_s, \omega), \quad (18)$$

in the Fourier space where $q_d$, q, and $q_s$ are conjugate variables of $\rho_d$, $\rho$, and $\rho_s$, respectively, and "*" denotes a complex conjugate. This yields a solution for $\Delta z_i(q)$ shown in Equation 19 below.

$$\Delta z_i(q) = \frac{1 - j\omega\tau_i}{\gamma_i c} \frac{U_{m_i}(q - q_s, q_s, \omega)}{G_m(q - q_s, \omega) G_x^*(q_s, \omega)_{m_i}} \quad (19)$$
$$= \frac{1 - j\omega\tau_i}{\gamma_i c} \frac{U_{m_i}(q_d, 0, \omega) \gamma_i c}{G_m(q_d, \omega) G_x^*(0, \omega)},$$

Please note, $q_s$ was chosen to be equal to 0, because usually there are much fewer sources than detectors (e.g., in the present embodiment where a CCD camera is used to detect the light emission at the surface illuminated by a single laser source 120 as shown in FIG. 1). An inverse Fourier transform of $(\Delta z_i(q))$ yields a thickness profile of the fluorescent target in the z direction. The FWHM (full width at half maximum value) and the contour of the thickness profile provide an estimation of size and shape of the ith target, respectively.

According to the present invention using OPTICA, virtual sources are assumed to be mutually independent and a specific light propagation model is not assumed. Appropriate light propagation models including the diffusion approximation, the cumulant approximation (e.g., see W. Cai, M. Lax and R. R. Alfano, "Analytical Solution Of the Elastic Boltzmann Transport Equation In An Infinite Uniform Medium Using Cumulant Expansion," J. Phys. Chem. B, vol. 104, no. 16, pp. 3996-4000, (2000); and M. Xu, W. Cai, M. Lax and R. R. Alfano, "A photon transport forward model for imaging in turbid media," Opt. Lett., vol. 26, no. 14, pp. 1066-1068, (2001), the contents of which are incorporated herein by reference), the random walk model (e.g., see A. H. Gandjbakhche et. al., "Photon Path-Length Distributions For Transmission Through Optically Turbid Slabs," Phys. Rev. E, vol.

48, no. 2, pp. 810-818, (1993) the contents of which are incorporated herein by reference), and radiative transfer can also be used with the OPTICA method according to the present invention. The number of targets within a medium is determined by the number of the independent components presented in a multi-source multi-detector data set contained within a turbid medium. Analysis of retrieved independent components from ICA then localizes and characterizes absorptive and/or scattering targets inside the turbid medium where an appropriate model of the light propagator is adopted. When a noise level is high and/or systematic errors are present, extra independent components may appear in readings. Only the leading independent components according to the respective contribution need to be analyzed to detect and characterize targets of interest and other components can be discarded.

Provided herein are several experiments which illustrate actual embodiments of the present invention in which OPTICA enables the detection and location of targets whose light absorption, scattering, or emission characteristic are different from that of a surrounding turbid medium. Absorptive, scattering, or fluorescent targets embedded in turbid media were used for experimental demonstration. A description of samples (e.g., specimens) used in the demonstration, experimental arrangement and procedures as well as experimental results will now be provided below.

Three tissue-simulating phantoms with absorption and scattering coefficients within the reported range of values emulating healthy human breast tissues and a fourth sample of (ex vivo) human breast tissue was used for following experiments (e.g., see H. Heusmarin et. al., "Characterization Of Female Breasts In vivo By Time Resolved And Spectroscopic Measurements In Near Infrared Spectroscopy", J. Biomed. Opt., vol. 1, pp. 425-434, (1996), the contents of which are incorporated herein by reference).

Figure 2:
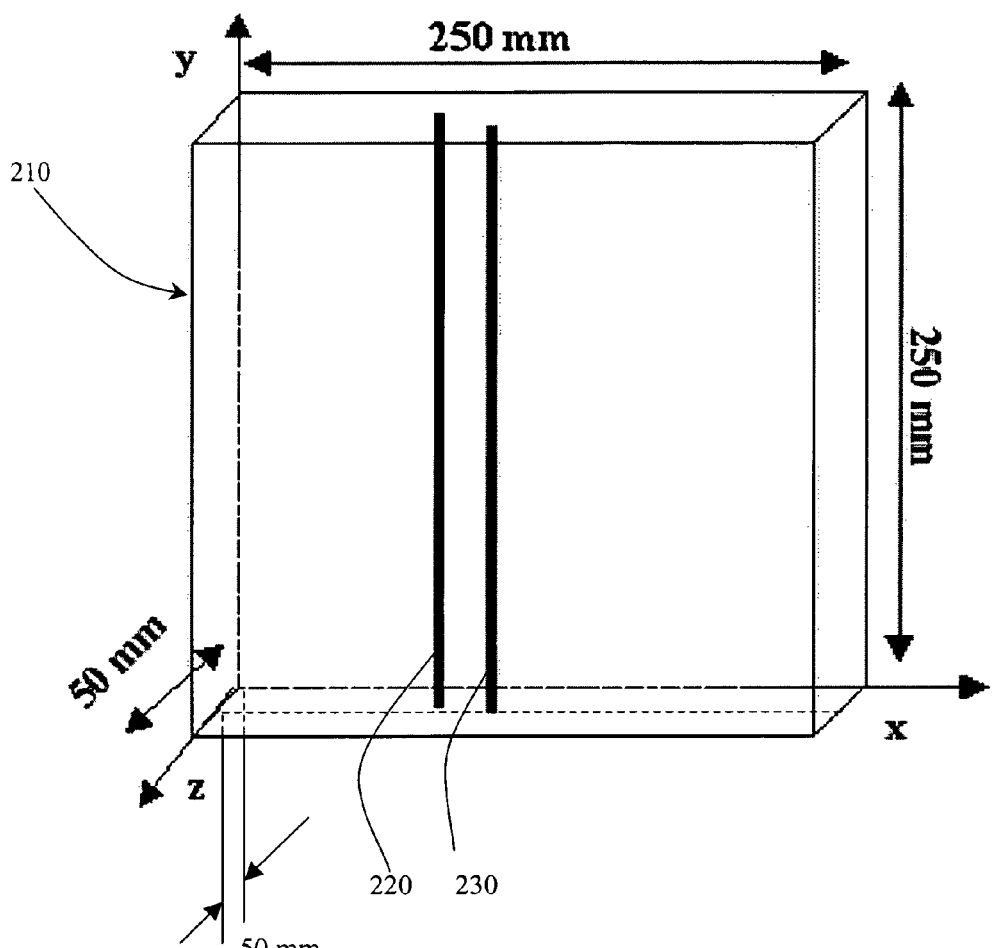
FIG. 2. is a diagram of a first specimen including an Intralipid-10% suspension in water and two long cylindrical absorbing objects having an absorption coefficient 0.23 $mm^{-1}$ according to an embodiment of the present invention.

A diagram of illustrating a first specimen including an Intralipid-10% suspension in water with two cylindrical absorbing objects having an absorption coefficient of 0.23 mm$^{-1}$ is shown in FIG. 2.

The first specimen 200 includes a 250 mm×250 mm×50 mm transparent plastic container (for forming a slab) 210 (which is similar to the sample 410 shown in FIG. 1) filled with Intralipid-10% suspension in water (not shown) with two absorbing targets 220 and 230, respectively, embedded in the container 210. The concentration of Intralipid-10% was adjusted (e.g., see Hugo J. van Staveren et. al., "Light Scattering In Intralipid-10% In The Wavelength Range Of 400-1100 nm", App. Opt., vol. 30, no. 31, PP. 4507-4514, (1991), the contents of which are incorporated herein by reference) to provide a transport length $l_t$ ~1 mm at 785 nm.

The absorbing targets 220 and 230 each include an 8-mm diameter 250-mm long cylindrical glass tube filled with a Intralipid-10% suspension (to provide the same scattering coefficient as the Intralipid-10% suspension) and an absorbing-ink solution for changing the absorption coefficient to 0.23 mm$^{-1}$. The absorbing targets 220 and 230 were placed at different depths along the 50 mm path length (i.e., the depth corresponding to the z-axis) of the plastic container 210.

Figure 3:
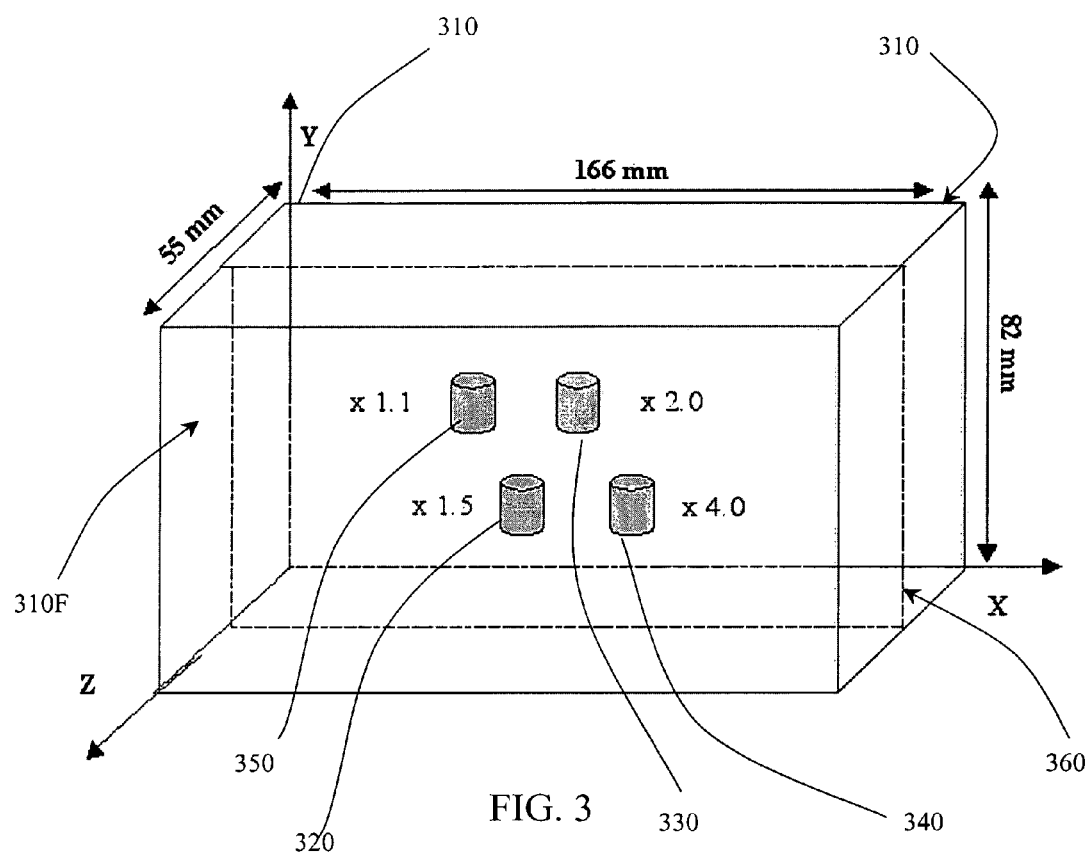
FIG. 3 is a diagram of a second specimen including a solid block formed from a scattering material in which four scattering cylindrical targets having their centers on the central plane are embedded.

A diagram illustrating a second specimen including a plurality of cylindrical scattering objects is shown in FIG. 3. The second specimen 300 includes a 166-mm long, 82-mm wide, and 55-mm thick slab 310 formed from materials having a reduced scattering coefficient $\mu'_s$~0.9 mm$^{-1}$ (transport length, $l_t$ ~1.1 mm), and an absorption coefficient, $\mu'_a$ ~0.006 mm$^{-1}$. The slab 300 includes four 5-mm diameter by 5-mm long cylindrical scattering targets 320, 330, 340, and 350. The center of each cylindrical scattering object (i.e., 320, 330, 340, and 350) is located in a plane 360 which is located halfway between a front side 310F and a back side 310 F of the slab 310. The absorption coefficient of each cylindrical scattering object 320, 330, 340, and 350, is 0.006 mm$^{-1}$, which is the same as that of the material of the slab 310, but the scattering coefficient of each cylindrical scattering object 320, 330, 340, and 350 is respectively 1.5, 2.0, 4.0, and 1.1 times greater than the scattering coefficient of the slab 310. The first and the third cylinders, and the second and the fourth cylinders are on two horizontal lines about 22 mm apart. The distance between neighboring cylinders is 11 mm. Further details about similar slabs may be obtained in D. J. Hall, et al. "Imaging Very-Low-Contrast Objects in Breastlike Scattering Media With A Time-Resolved Method", Appl. Opt., vol. 36, pp. 7270-7276, (1997), the contents of which are incorporated herein by reference.

A perspective view diagram illustrating a third specimen is shown in FIG. 3. The third specimen is also shown in FIG. 1 The third specimen 400 includes a spherical fluorescent target 420 placed inside a slab 410 measuring 250 mm×250 mm×50 mm, which is similar to the size and the composition of the slab 210 and 310 shown in the first and second specimens, respectively. The slab 410 is filled with an Intralipid-10% aqueous suspension. The fluorescent target 400 includes a 9.0 mm diameter sphere filled with a solution in water and Indocyanine green (ICG) dye that can be ex cited in the 650 nm-800 nm spectral range.

A fourth specimen (not shown) includes a spherical fluorescent target placed inside an ex vivo human breast tissue sample. The tissue sample was assembled as a 26 mm thick, 50 mm long and 50 mm wide slab slightly compressed between two glass plates. The fluorescent target was a 4.0 mm-diameter glass sphere filled with ICG solution in water. The experimental setup is the similar to the setup used by the third specimen and will not be further discussed for the sake of clarity.

Referring back to FIG. 1, an experimental setup for analyzing a slab (e.g., the third specimen 400) will now be discussed in further detail. An optical source (e.g., a laser) provides incident light beams having a wavelength of $\lambda_x$=785 nm. Two (optional) long wavelength pass absorption filters 150-1 and 150-2 were placed between the Fluorescent target 410 and the CCD camera unit 120 to block the excitation wavelength and allow fluorescence light to pass. The wavelength of the peak fluorescence light adjusted by the filtering and the CCD camera 120 response efficiency is about $\lambda_m$=870 nm. The Intralipid-10% suspension is diluted with pure water such that the transport mean free paths and absorption coefficients are $l_{t_x}$=1.01 mm and $\mu_{a_x}$=0.0022 mm$^{-1}$ at the excitation wavelength, and $l_{t_m}$=1.14 mm and $\mu_{a_m}$=0.0054 mm$^{-1}$ at the emission wavelength, respectively. Sample targets 180 are shown for illustration purposes only and are not included with the third sample slab 400 in actual embodiments.

The experimental arrangement shown in FIG. 1 can be used for imaging of specimens, including the first to fourth specimens, etc. For CW measurements a 200-μm fiber 170 delivers a beam of 784-nm light from a diode laser 180 (e.g., an Ocean Optics R-2000) illuminates an input surface (or source plane) 110 of the specimen 410. A cooled CCD camera 120 set to an acquisition time of 150-ms records two-dimensional (2-D) intensity patterns of the light transmitted through the opposite side of the slab specimen 410 (i.e., the side adjacent to a detector plane 190). For time-resolved measurements a 1-mm diameter collimated beam of 785-nm, 150-fs, 1-kHz repetition rate light pulses from a Ti:sapphire laser and amplifier system (e.g., see Q. Fu et. al. "High-average-power kilohertz-repetition-rate sub-100-fs Ti-sapphire amplifier system", Opt. Lett, vol. 22, pp. 712-714, (1997)) can be used to illuminate the sample (e.g., fluorescent sample 410). An ultrafast gated intensified camera system (UGICS) that provides an FWHM gate width variable from 80 ps to 6 ns can be used to record 2-D intensity patterns of the light transmitted through the opposite side of the slab.

Computer controlled xy translation stages were used for scanning the specimens in an array of points in the xy plane as displayed in FIG. 3. The computer controlled xy translation stages is adjusted according to variables which can include the number of expected targets and the size, shape, and type of expected targets. For example, for the long cylindrical absorbing targets included in the first specimen, a line scan of 16 points with a step size of 2.5 mm along x-axis is used to obtain (x, z) locations of the absorbing cylinders. Using the second specimen, an array of 20×18 points with a step size of 2.5 mm across the lateral positions of the 4 scattering targets was used for scanning to obtain the locations of the 4 scattering targets. Using the third specimen, point source scans over a 10×10 grid system with spacing of 2.5 mm between consecutive grids, was used to establish the position the fluorescent target.

Using the previously described methods and targets, temporal profiles of the transmitted pulses were generated using the UGICS in the scan mode with an 80-ps gate width. Average optical properties of the turbid medium were estimated by fitting the temporal profiles to the diffusion approximation of the radiative transfer equation (RTE).

ICA of the perturbations in the spatial intensity distributions provided corresponding independent intensity distributions on the source and detector planes. ICA generated independent intensity distributions on the source and detector planes are shown in diagrams (a) and (b) of FIG. 4 respectively, for the two absorbing cylinders of the first specimen. Locations of the absorbing cylinders are obtained by fitting independent component intensity distributions to those of the diffusion approximation in a slab using Equation 6. In actual experiments, the first cylinder was determined to be located at x=24 mm, 29 mm away from the source plane and 21 mm away from the detector plane, and the location was determined to be second cylinder at x=47 mm, 33 mm away from the source plane and 17 mm away from the detector plane. The experimentally obtained (x and z) coordinates of both of the cylinders are within 0.5 mm of their actual known positions.

Figure 5:
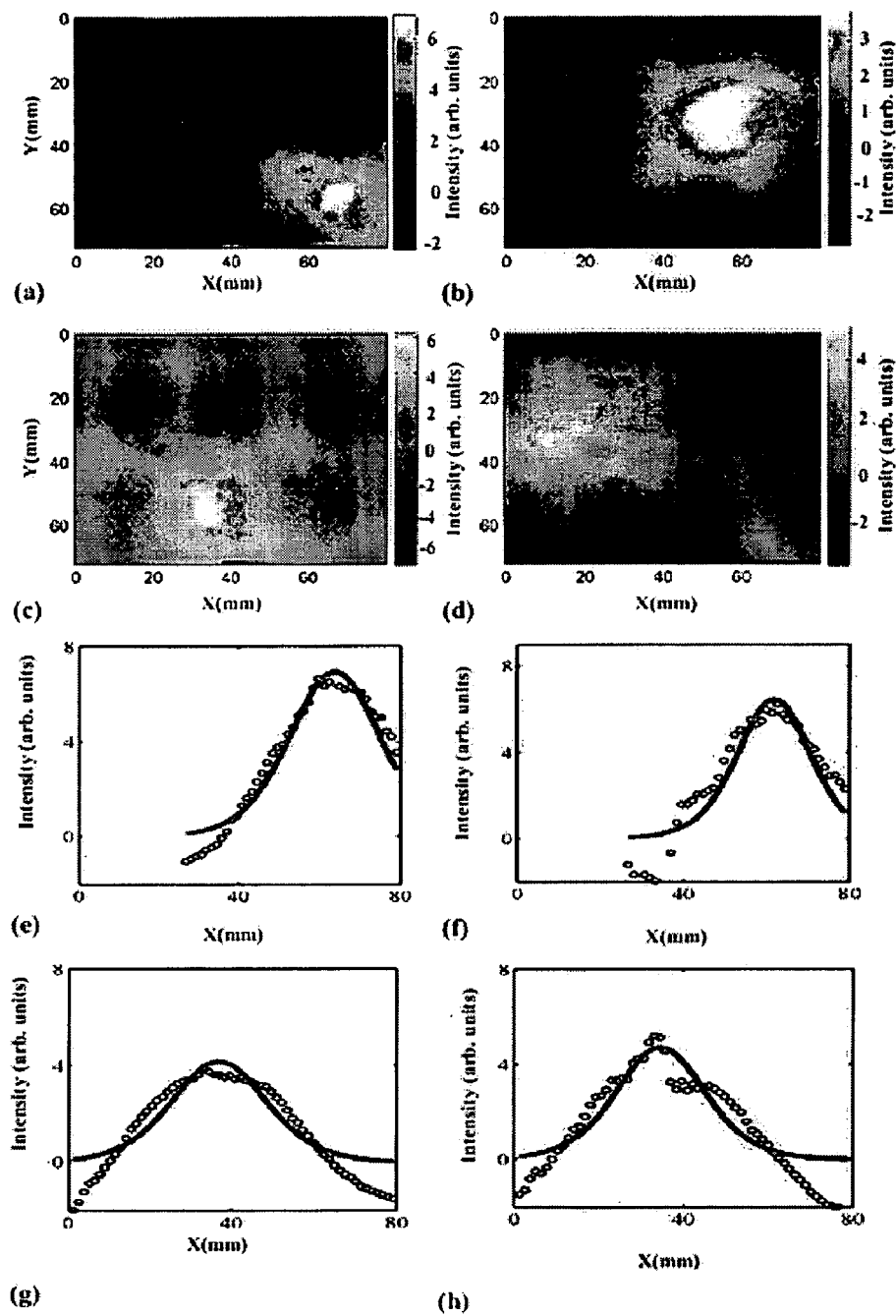
FIG. 5 shows light intensity patterns and graphs respectively illustrating independent spatial intensity distributions at the exit (or detector) plane generated by ICA corresponding to objects with scattering coefficients of 4 times, 2 times, 1.5 times, and 1.1 times of that of the material of the slab of the second specimen.

Independent intensity distributions at the detector plane corresponding to the four scattering targets of the second specimen are displayed in diagrams (a)-(d) of FIG. 5. These independent intensity distribution components are then used to obtain projections of a target-detector Green's function, $G(r_d, r_j)$, with $j=1, 2, 3, 4$, on the detector plane for the four small cylindrical scattering targets embedded in the second specimen. Locations of the targets are determined by fitting the projections to those of the model Green's function e.g., see diagrams (e)-(h) of FIG. 5. Locations of all four targets were then experimentally determined. Even the weakest scatterer, with a scattering coefficient just 11.1 times the background and hence considered to be rather unlikely to be found e.g., see Davie J. Hall et. al., "Imaging Very-Low-Contrast Objects in Breastlike Scattering Media With a Time-Resolved Method", Appl. Opt., vol. 36, pp. 7270-7276, 1997), were detected. The known and OPTICA estimated positions of the four objects are presented in Table 1 below. As shown in Table 1, positions along z-axis (depth) of the cylinders were experimentally determined to be located at 28.13 mm, 27.87 mm, 27.08 mm and 32.6 mm. Except for the experimental results for the last cylinder, the depth of other cylinders agree within 1 mm of their known center positions of 27.5 mm. The OPICA-estimated lateral positions of each of the other targets was within 2-3 mm of the actual lateral positions of each respective target.

TABLE 1

| Target | Target Strength | Known Position (x, y, z) (mm) | OPTICA Estimated Position (x, y, z) (mm) |
|---|---|---|---|
| #1 | 4 | (60, 60, 27.5) | (62, 63, 28.13) |
| #2 | 2 | (47, 30, 27.5) | (48, 33, 27.87) |
| #3 | 1.5 | (33, 60, 27.5) | (33, 62, 27.08) |
| #4 | 1.1 | (20, 30, 27.5) | (18, 33, 32.6) |

Figure 6:
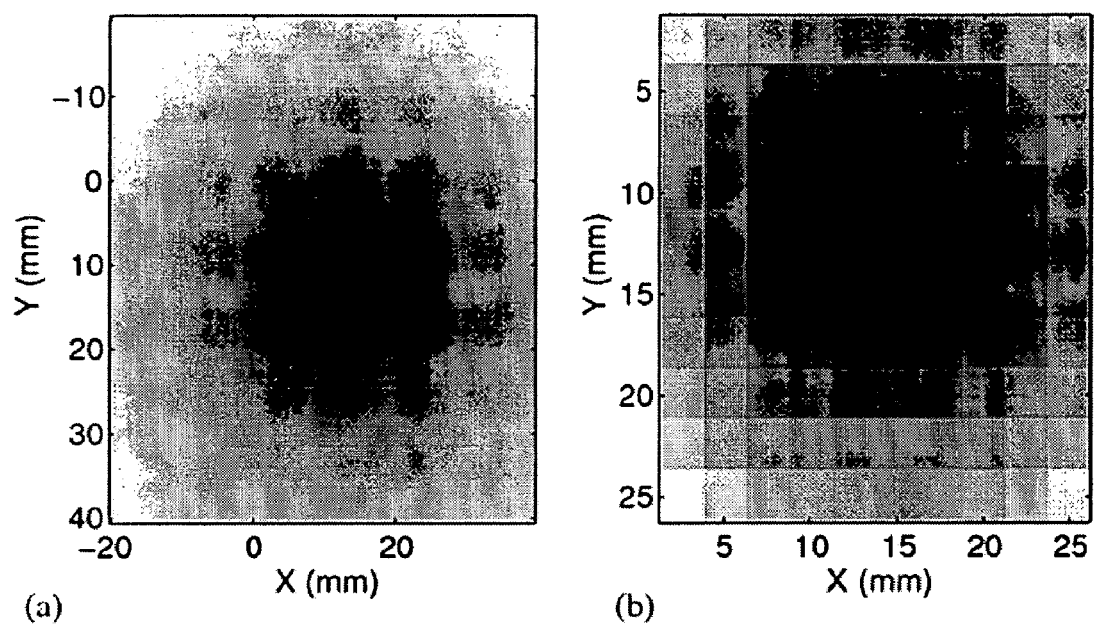
FIG. 6 shows graphs illustrating independent intensity distributions of the fluorescence from the target generated by ICA at the detector plane and at the source plane.

Independent intensity distributions at the detector plane and the source plane obtained by ICA for the third specimen 3 is shown in FIG. 6. The fluorescent target is found to be z=33 mm away from the input window by fitting independent intensity distributions at the detector plane and the source plane to the respective Green's functions (e.g., see diagrams (a) and (b) of FIG. 7). This agrees with the input value z=32 mm away from the input window. The thickness map is obtained using Equation 19 and presented in diagram (c) of FIG. 7 while the horizontal and vertical thickness profile of $\Delta_z/Z_{max}$ are also plotted in diagram (d) of FIG. 7. The target is found to be centered at (x=11, z=9) mm and have a circular shape. The FWHM of the peak found to be d=11.5 mm. This value should be compared to the diameter of the fluorophore 9 mm.

Figure 8:
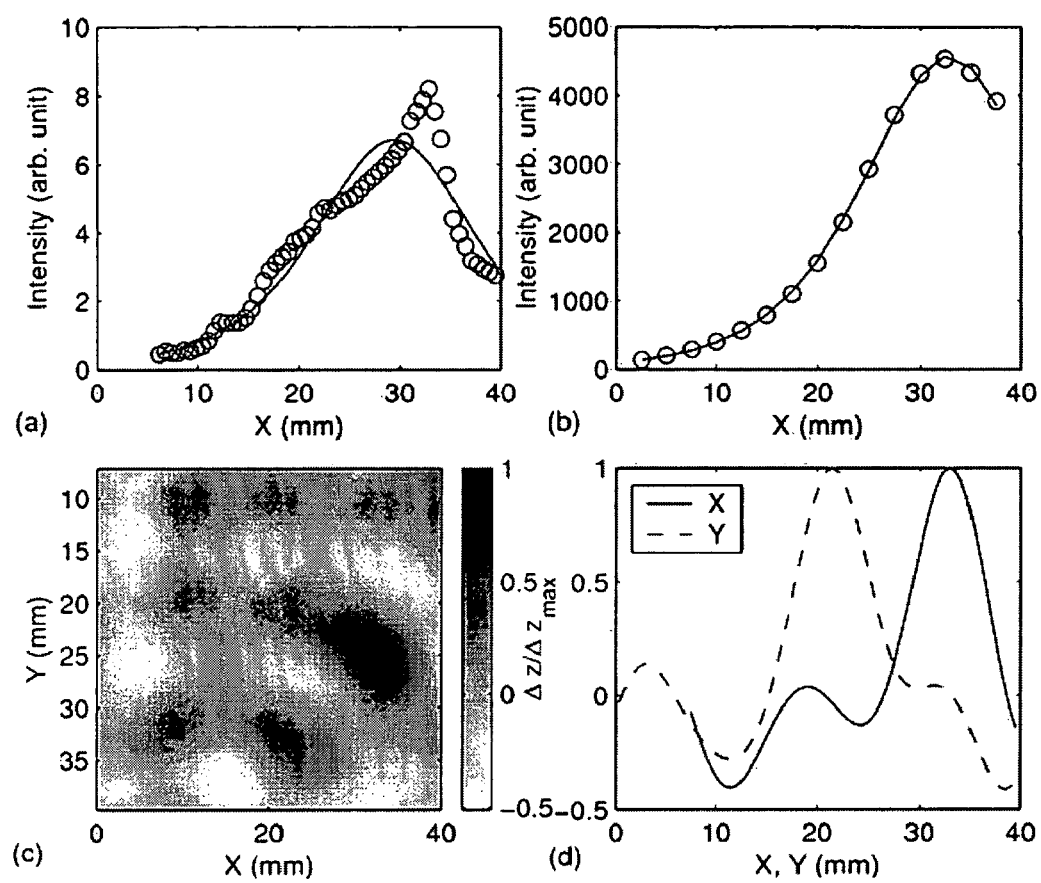
FIG. 8 shows are graphs illustrating fitting of the independent intensity distribution of fluorescence from a sphere of diameter 4 mm embedded in 26 mm thick human breast tissue to the model Green's function.

The fluorescent target in the fourth sample is found to be z=11 mm away from the input window by fitting independent intensity distributions at the detector plane and the source plane to the respective Green's functions (see diagrams (a) and (b) of FIG. 8). This agrees well with the input value z~10 mm away from the input window. The thickness map is obtained using Equation 19 and presented in diagram (c) of FIG. 8 while the horizontal and vertical thickness profile of $\Delta_z/_{zmax}$ are also plotted in diagram (d) of FIG. 8. The target is found to be centered at (21, 33) mm and have a circular shape. The FWHM of the peak is found to be d=7.1 mm. This value should be compared to the diameter of the fluorophore 4 mm.

The experimental results demonstrate that the present invention using OPTICA, can successfully detect and obtain the location of absorbing, scattering, and/or fluorescent targets embedded inside a turbid medium. 4 mm targets located deep within a thick human breast tissue have been shown to be successfully located within an error of several millimeters and characterized in experiments. Accordingly, the present invention using OPTICA can be used to detect and obtain the location of absorbing, scattering, and/or fluorescent targets of 1 mm size embedded inside a turbid medium.

Figure 4:
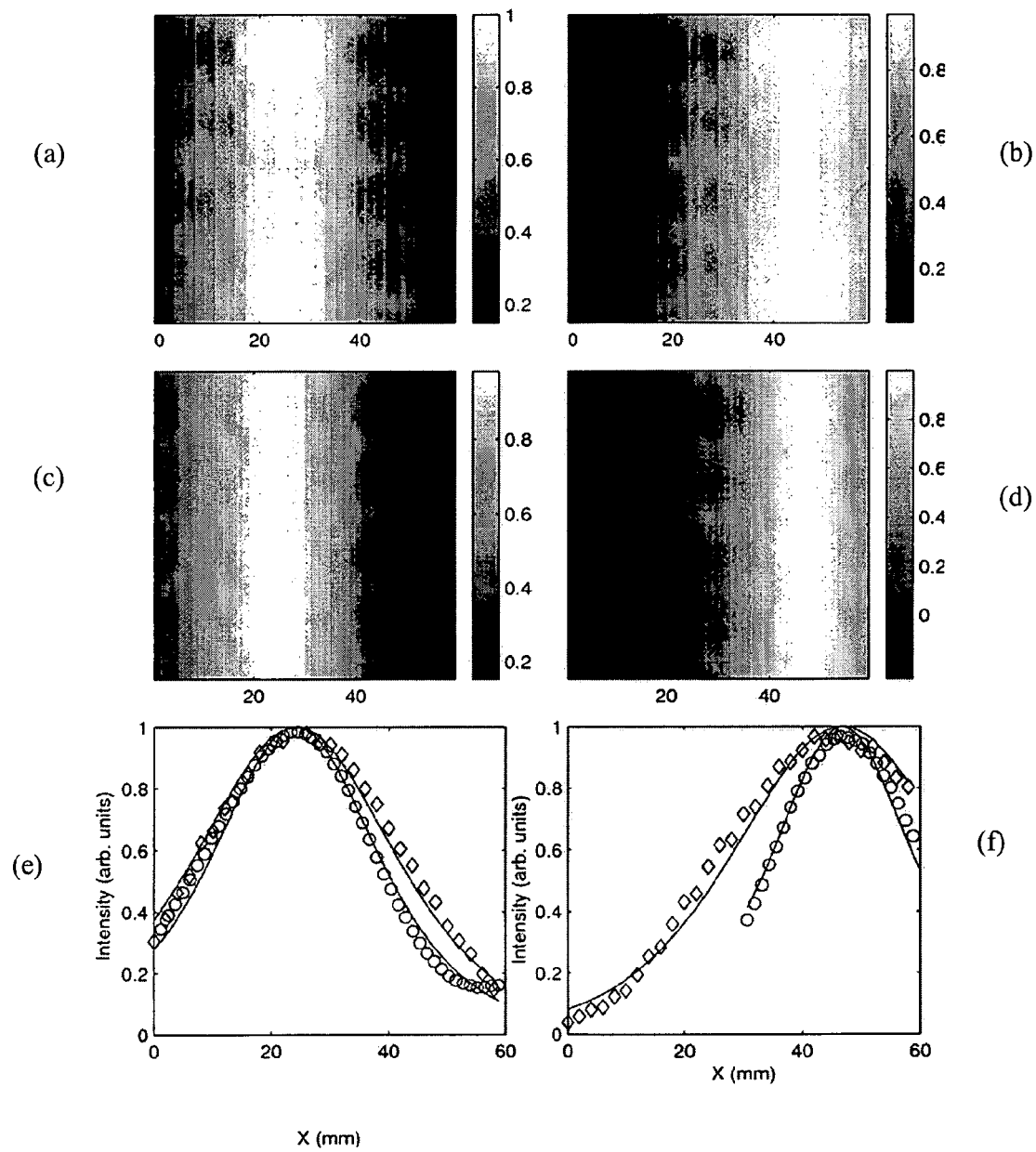
FIG. 4 shows light intensity patterns and graphs illustrating normalized independent spatial intensity distributions as a function of the lateral position x at the input (or source) plane (first row) and the exit (or detector) plane (the second row) generated by ICA and a horizontal profile of intensity distributions on the source plane (illustrated by diamonds) and on the detector plane (illustrated by circles) are displayed on the third row for the two absorbing cylinders of the first specimen.

Graphs illustrating normalized independent spatial intensity distributions as a function of the lateral position x at the input (or source) plane (first row) and the exit (or detector) plane (the second row) generated by ICA and a horizontal profile of intensity distributions on the source plane (illustrating diamonds) and on the detector plane (illustrating using circles) are displayed on the third row for the two absorbing cylinders of the first specimen is shown in diagrams (a)-(f) of FIG. 4. Solid lines illustrate the respective Green's function fit used for obtaining locations of objects.

Graphs illustrating independent spatial intensity distributions at the exit (or detector) plane generated by ICA corresponding to objects with scattering coefficients: (a) 4 times, (b) 2 times, (c) 1.5 times, and (d) 1.1 times of that of the material of the slab in the second specimen are shown in diagrams (a)-(h) of FIG. 5. Horizontal profiles of intensity distributions shown in diagrams (a)-(d) of FIG. 5 are illustrated by circles in diagrams (e) and (f) of FIG. 5, respectively, with solid lines representing the Green's function fit used for extracting object locations.

Graphs illustrating independent intensity distributions of the fluorescence from the target generated by ICA at the detector plane and the source plane, are illustrated in diagrams (a)-(b) of FIG. 6, respectively.

Figure 7:
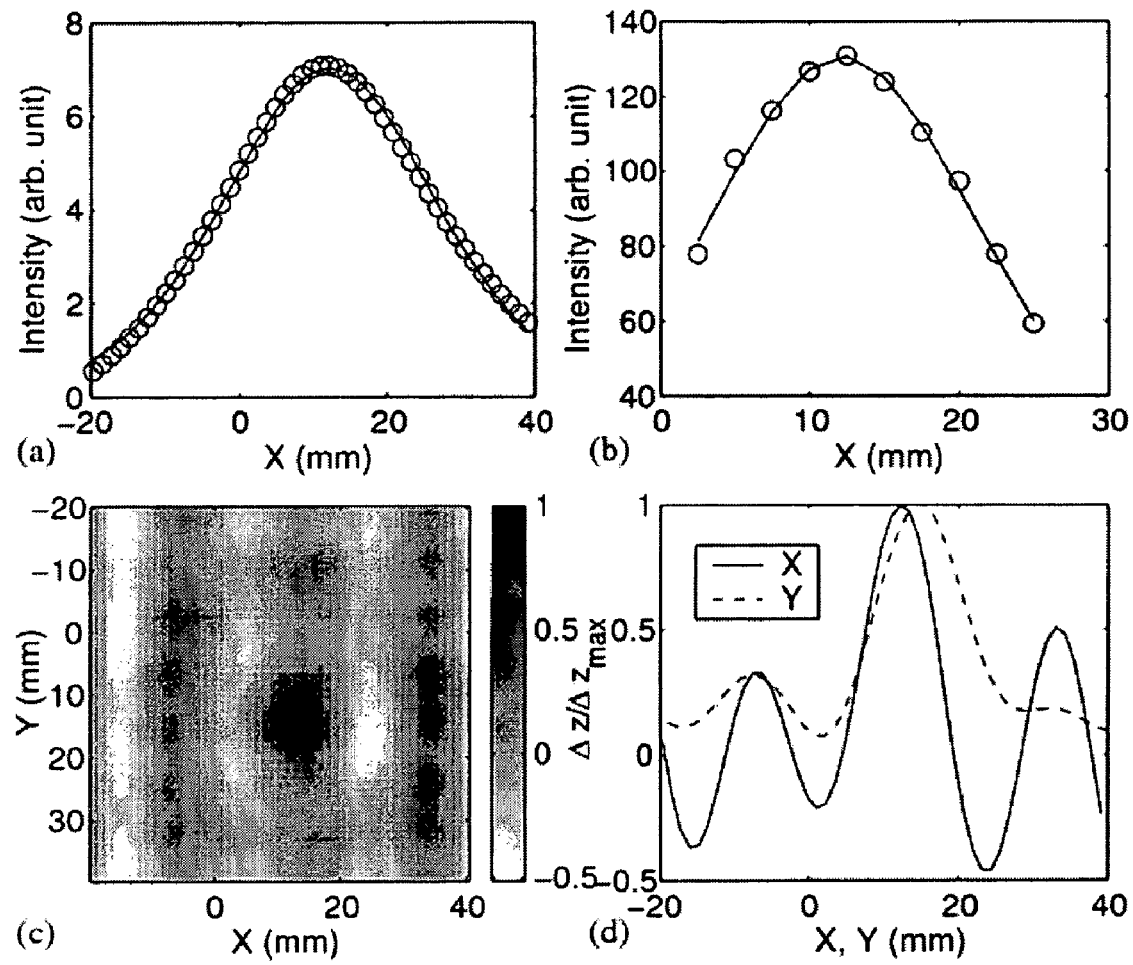
FIG. 7 shows graphs illustrating fitting of the independent intensity distribution of fluorescence from a sphere of diameter 9 mm embedded in Intralipid-10% solution to the model Green's function.

Graphs illustrating fitting of the independent intensity distribution of fluorescence from a sphere of diameter 9 mm embedded in Intralipid-10% solution to the model Green's function are shown in diagrams (a)-(c) of FIG. 7. The independent intensity distribution of fluorescence from a sphere of diameter 9 mm embedded in Intralipid-10% solution to the model Green's function are at the detector plane and at the source plane are illustrated in diagrams (a) and (b) of FIG. 7, respectively. The thickness map of the target centered at (11, 9) mm and the thickness profiles along X and Y directions, are illustrated in diagrams (c) and (d) of FIG. 7, respectively.

Graphs illustrating fitting of the independent intensity distribution of fluorescence from a sphere of diameter 4 mm embedded in human breast tissue to the model Green's function is illustrated in diagrams (a)-(c) of FIG. 8. The independent intensity distribution of fluorescence from a sphere of diameter 4 mm embedded in human breast tissue to the model Green's function at the detector plane and at the source plane, are illustrated in diagrams (a) and (b) of FIG. 8, respectively. A thickness map of the target centered at (21, 33) mm, and a thickness profiles along X and Y directions, are shown in diagrams (c) and (d) of FIG. 8, respectively.

Figure 9:
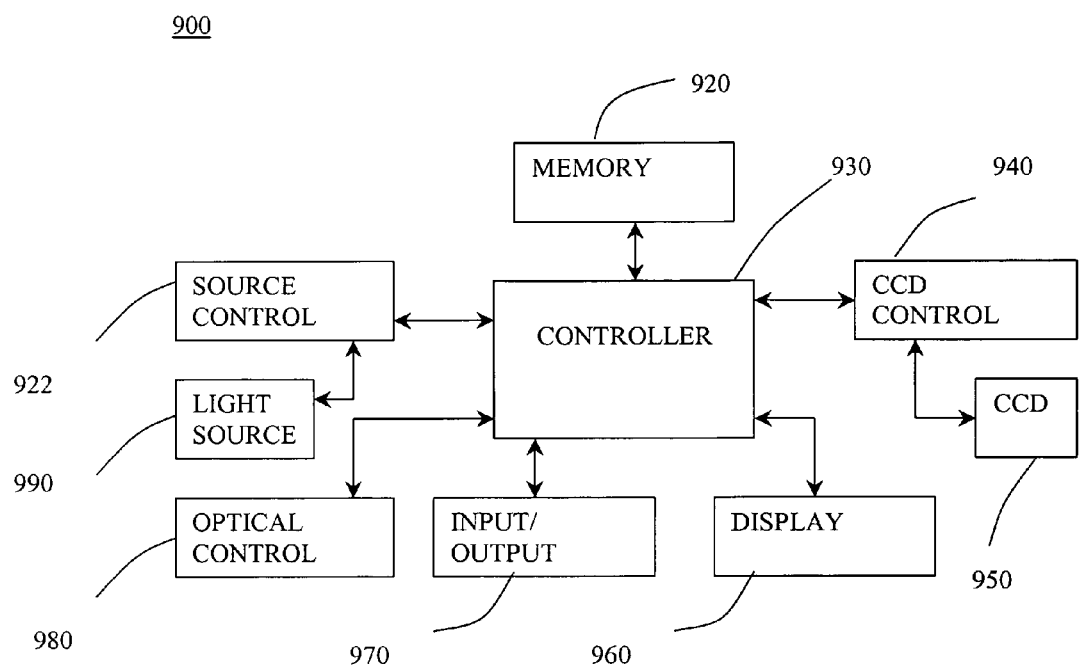
FIG. 9 is a block diagram illustrating a control system for controlling the experimental arrangement shown in FIG. 1.

FIG. 9 is a block diagram illustrating a control system for controlling the experimental arrangement shown in FIG. 1 according to an embodiment of the present invention. The system 900 includes a controller 930, a CCD control unit 940, a CCD camera 950, an display unit 960, an input/output device 970, an optical control unit 980, a light source unit 990, an source control unit 922, and a memory unit (e.g., RAM, ROM, FLASH, etc.) 920. The controller 930 controls the overall operation of the system 900 and stores data and retrieves necessary data (e.g., operating instructions, data generated during use, etc.) in the memory unit 920. The CCD control unit 940 interacts with the controller 930 and controls the operation of the CCD camera 950. The display 960 receives data from the controller (and/or other device such as a CCD camera, etc.) and displays the data. The input/output unit 970 can include a mouse, a keyboard, a touch-screen, etc. (not shown) for entering commands from a user, and other devices (e.g., a network connection for communicating with a LAN/WAN, the Internet, etc., and an optional external memory) for controlling the operation of the system 900. The optical control unit 980 is controls the location of incident light relative to a source plane. For example, optical control unit 980 can be used to focus and/or locate incoming (incident) light as desired using lenses and mirrors, respectively, which are controlled by stepper motors, etc. The source control unit 922 is operated by the controller 930 and controls the light source 990. The light source 990 can include a laser or other suitable device for producing a desired incident beam and can preferably produce an incident beam having a given wavelength and duration. The controller 930 (and/or other devices shown in FIG. 9 can be included within a Personal Computer (PC) 190 shown in FIG. 1. In other embodiments, optical sources and detectors can be remotely located and operated by one or more controllers. In yet other embodiments, a plurality of light sources (e.g., a plurality of light-emitting-diode (LED) lasers can be used in which case the source an optical control system for locating an incident beam may not be necessary.

Figure 10:
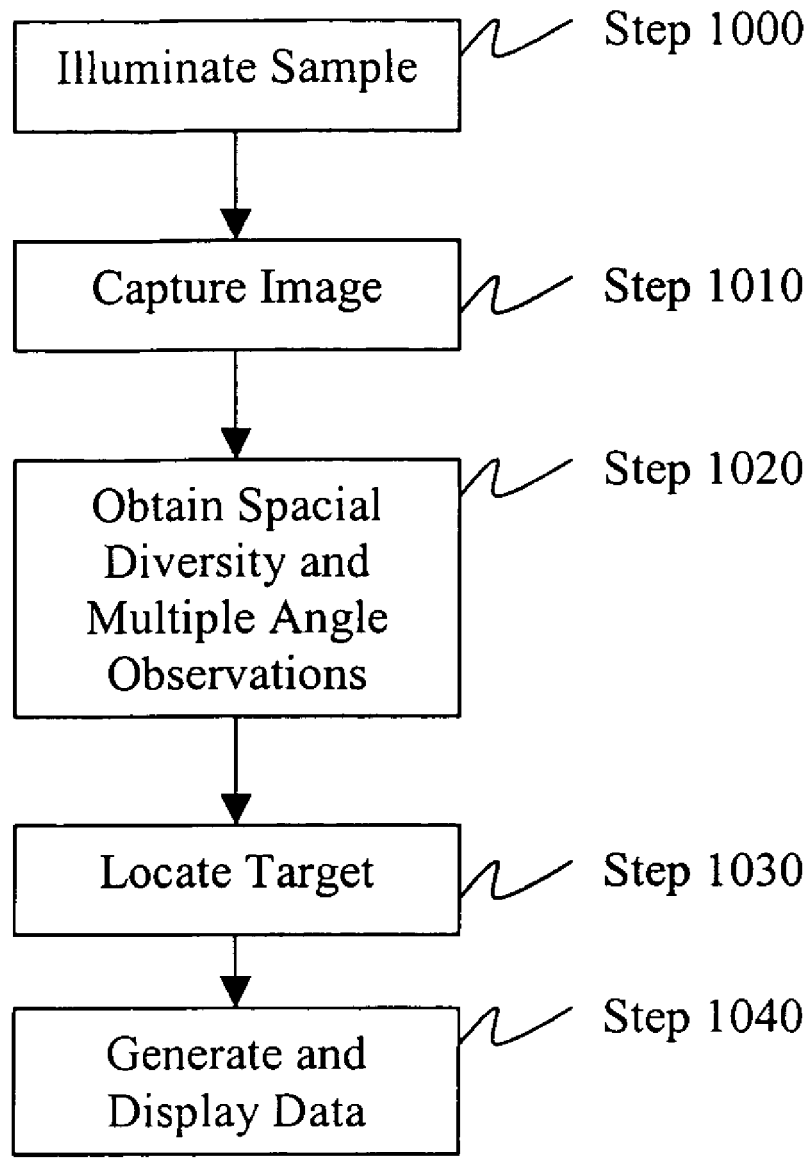
FIG. 10 is a flow chart illustrating the operation of an embodiment of the present invention for locating a target location.

FIG. 10 is a flow chart illustrating the operation of an embodiment of the present invention for locating a target location. In Step 1000 a sample is illuminated by the light source. In Step 1020, a camera (e.g., a CCD camera) captures an image of the illuminated sample. In Step 1030 resulting special diversity and multiple angle observations are obtained. In Step 1040 a target located within the sample is located and characterized using a comparison to a prototype Greens function. In Step 1050 generated data is displayed on a display.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method for detecting a presence of one or more objects in a turbid medium, comprising:

illuminating, by a light source, at least a portion of the turbid medium with incident light having at least one predetermined wavelength which interacts with the one or more objects contained in the turbid medium differently than the incident light interacts with the turbid medium;

measuring, by one or more light detectors, light that emerges from the turbid medium;

detecting and locating, by a processor, the one or more objects located within the turbid medium based on an Optical Imaging Independent Component Analysis (OPTICA) of the emergent light from the turbid medium; and extracting three-dimensional location information about the objects from the processor, wherein the incident light includes at least two different wavelengths, measurements are made at different wavelengths to obtain at least two signals $I_{\lambda_1}$ and $I_{\lambda_2}$, which are compared and correlated, and information about the one or more objects inside the turbid medium is extracted by processing the results of the comparison and correlation.

2. The method as claimed in claim 1, wherein, the light that emerges from the turbid medium has a same wavelength as the incident light, is detected using a light detector, and is analyzed using the OPTICA to determine independent components, and wherein a location of the one or more objects is obtained based on knowledge of the independent components.

3. The method as claimed in claim 1, wherein the light that emerges includes a plurality of wavelengths, at least one of the wavelengths being different from the at least one wavelength of the incident light.

4. The method as claimed in claim 2, wherein the light that emerges includes a plurality of wavelengths, at least one of the wavelengths being different from a wavelength of the incident light.

5. The method as claimed in claim 1, wherein the light source includes at least one of a light pulse, a continuous-wave light, an amplitude modulated light, and a laser light.

6. The method as claimed in claim 1, wherein the at least one wavelength includes wavelengths between 700 nm and 1500 nm.

7. The method as claimed in claim 1, wherein the at least one wavelength of the illuminating light includes wavelengths between 750 nm and 950 nm, and is produced by the laser selected from one of a Ti:sapphire laser, a dye laser, a semiconductor laser, and a solid-state laser.

8. The method as claimed in claim 1 wherein the at least one wavelength of the illuminating light includes wavelengths between 950 nm and 1150 nm, and is produced by the laser selected from one of a Nd:YAG laser, a semiconductor laser, and a solid-state laser.

9. The method as claimed in claim 1 wherein at least one wavelength of the illuminating light includes wavelengths between 1150 nm and 1500 nm, and is produced by the laser selected from one of a $Cr^{4+}$-based laser, a semiconductor laser, and a color-center laser.

10. The method as claimed in claim 5 wherein the illuminating light having at least one wavelength is produced by a laser having a variable wavelength.

11. The method as claimed in claim 1, wherein one or more objects are one of an absorptive target having and absorption coefficient different from the turbid medium, a scattering target having a scattering coefficient different from the turbid medium, and an emissive target emitting light having at least one wavelength which is different than the wavelength of the incident light.

12. The method as claimed in claim 2, wherein the light detector includes one of a charge-coupled device (CCD) camera, a near-infrared area camera, a one-dimensional array of detectors, photodiodes, photomultiplier tubes, and a streak camera.

13. The method as claimed in claim 1, further comprising discriminating noise due to at least one of multiple scattered light and ambient background by using a gating method.

14. The method as claimed in claim 13, wherein the gating method includes at least one of space gating, Fourier gating, time gating, polarization gating, confocal gating, nonlinear optical gating, and coherence gating.

15. The method as claimed in claim 14, wherein an electronically controlled timed gate is used for the time gating.

16. The method as claimed in claim 15, wherein the electronically controlled time gate includes at least one of an ultrafast gated intensified camera system (UGICS) having a gated image intensifier coupled to a charge-coupled-device (CCD) camera.

17. The method as claimed in claim 16, wherein at least one of duration and position of the time gate is variable.

18. The method as claimed in claim 14, wherein time gating is provided by one of an optical Kerr gate, a second harmonic generation cross correlation gate, a four-wave mixing gate, and an upconversion gate.

19. A system for detecting a presence of one or more objects in a turbid medium, comprising:
   a light source configured to illuminate at least a portion of the turbid medium with incident light having at least one predetermined wavelength which interacts with the one or more objects contained in the turbid medium differently than the incident light interacts with the turbid medium;
   an image capture device configured to measure light that emerges from the turbid medium; and
   a processor configured to detect the presence and determine the three-dimensional location of the one or more objects located within the turbid medium based on an Optical Imaging Independent Component Analysis (OPTICA) of the emergent light from the turbid medium,
   wherein the incident light includes at least two different wavelengths, measurements are made at different wavelengths to obtain at least two signals $I_{\lambda_1}$ and $I_{\lambda_2}$, which are compared and correlated, and information about the one or more objects inside the turbid medium is extracted by processing the results of the comparison and correlation.

20. The system as claimed in claim 19, further comprising a light detector for detecting the light that emerges from the turbid medium,
   wherein the light emerging from the turbid medium has at least one wavelength which is the same as a wavelength of the incident light, and is analyzed using the OPTICA to determine independent components, and
   wherein the processor obtains the location of the one or more objects based on the independent components.

21. The system as claimed in claim 19, wherein the emergent light includes a plurality of wavelengths with at least one of the emergent wavelengths being different from the wavelengths of the incident light.

22. The system as claimed in claim 19, wherein the light detector includes one of a CCD camera, a near-infrared area camera, a one-dimensional array of detectors, photodiodes, photomultiplier tubes, and a streak camera.

23. A system for detecting a presence of a tumor in a turbid medium formed of another type of tissue, comprising:
   a light source configured to illuminate at least a portion of the turbid medium with incident light having at least one wavelength which interacts with the tumor differently than the light interacts with the turbid medium;
   an image capture device configured to capture and measure light that emerges from the turbid medium, the turbid medium at least partially surrounding the tumor; and
   a processor configured to detect and determine the three-dimensional location of the tumor based on an Optical Imaging Independent Component Analysis (OPTICA) of the emergent light from the turbid medium,
   wherein the incident light includes at least two different wavelengths, measurements are made at different wavelengths to obtain at least two signals $I_{\lambda_1}$ and $I_{\lambda_2}$, which are compared and correlated, and information about the one or more objects inside the turbid medium is extracted by processing the results of the comparison and correlation.

* * * * *